US010506985B2

(12) United States Patent
Gaudiuso et al.

(10) Patent No.: US 10,506,985 B2
(45) Date of Patent: Dec. 17, 2019

(54) METHODS AND SYSTEMS FOR DIAGNOSING OR MONITORING PROGRESS OF A PATHOLOGY USING LASER INDUCED BREAKDOWN SPECTROSCOPY AND BIOLOGICAL FLUIDS

(71) Applicant: The University of Massachusetts, Boston, MA (US)

(72) Inventors: Rosalba Gaudiuso, Lowell, MA (US); Ebo Ewusi-Annan, Lowell, MA (US); Noureddine Melikechi, Lowell, MA (US); Benyuan Liu, Lowell, MA (US)

(73) Assignee: The University of Massachusetts, Boston, MA (US)

( * ) Notice: Subject to any disclaimer, the term of this patent is extended or adjusted under 35 U.S.C. 154(b) by 0 days.

(21) Appl. No.: 16/008,444

(22) Filed: Jun. 14, 2018

(65) Prior Publication Data

US 2018/0360390 A1 Dec. 20, 2018

Related U.S. Application Data

(60) Provisional application No. 62/520,282, filed on Jun. 15, 2017.

(51) Int. Cl.
*G01J 3/30* (2006.01)
*A61B 5/00* (2006.01)
(Continued)

(52) U.S. Cl.
CPC .............. *A61B 5/7267* (2013.01); *A61B 5/02* (2013.01); *A61B 5/08* (2013.01); *A61B 5/20* (2013.01); *A61B 5/4325* (2013.01); *A61B 5/444* (2013.01); *G01N 21/718* (2013.01); *A61B 5/0071* (2013.01); *A61B 5/4088* (2013.01); *A61B 5/4222* (2013.01); *A61B 5/4842* (2013.01); *G01J 3/443* (2013.01)

(58) Field of Classification Search
CPC ....... A61B 5/7267; A61B 5/0071; A61B 5/02; A61B 5/08; A61B 5/20; A61B 5/4088; A61B 5/4222; A61B 5/4325; A61B 5/444; A61B 5/4842; G01J 3/443; G01J 3/718; G01N 2001/045
USPC ....................................................... 356/318
See application file for complete search history.

(56) References Cited

U.S. PATENT DOCUMENTS 5,991,653 A * 11/1999 Richards-Kortum ........................ A61B 5/0059
250/339.01
6,789,069 B1 9/2004 Barnhill et al.
(Continued)

FOREIGN PATENT DOCUMENTS

JP 2014044110 A 3/2014

OTHER PUBLICATIONS

Alaa Tharwat et al., "Linear discriminant analysis: A detailed tutorial", AI Communications 00, IOS Press, 2017.
(Continued)

*Primary Examiner* — Tarifur R Chowdhury
*Assistant Examiner* — Jonathon Cook
(74) *Attorney, Agent, or Firm* — Burns & Levinon LLP; Orlando Lopez

(57) ABSTRACT

Systems and methods for diagnosing or monitoring progress of a pathology using laser induced breakdown spectroscopy (LIBS) and machine learning are disclosed.

22 Claims, 13 Drawing Sheets

(51) Int. Cl.
   *A61B 5/08*   (2006.01)
   *A61B 5/02*   (2006.01)
   *A61B 5/20*   (2006.01)
   *G01N 21/71*  (2006.01)
   *G01J 3/443*  (2006.01)

(56) References Cited

U.S. PATENT DOCUMENTS

| | | | |
|---|---|---|---|
| 7,394,537 | B1 | 7/2008 | Lindfors et al. |
| 7,899,625 | B2 | 3/2011 | Bhanot et al. |
| 8,450,057 | B2* | 5/2013 | Gordon ............ G01N 33/57423 435/6.1 |
| 2003/0218747 | A1* | 11/2003 | Ramaseder ............ G01N 21/63 356/318 |
| 2004/0199079 | A1* | 10/2004 | Chuck .................. A61B 5/0059 600/477 |
| 2016/0116416 | A1* | 4/2016 | Wang .................... G01N 21/718 356/318 |
| 2018/0120205 | A1* | 5/2018 | Melikechi .............. G01N 21/63 |

OTHER PUBLICATIONS

J. Pohjalainen, et al., "Feature selection methods and their combinations in high-dimensional classification of speaker likability, intelligibility and personality traits", Computer Speech & Language, vol. 29, Issue 1, Jan. 2013.

Max Welling, "Fisher Linear Discriminant Analysis", https://www.ics.uci.edu/~welling/teaching/273ASpring09/Fisher-LDA.pdf (2009).

Nikolay Stanevski, et al., "Using Support Vector Machine as a Binary Classifier", International Conference on Computer Systems and Technologies—CompSysTech' 2005.

R. Gaudiuso, et al., "Using LIBS to diagnose melanoma in biomedical fluids deposited on solid substrates: Limits of direct spectral analysis and capability of machine learning", Spectrochimica Acta Part B 146 (2018).

N. Melikechi, et al., "Age-specific discrimination of blood plasma samples of healthy and ovarian cancer prone mice using laser-induced breakdown spectroscopy", Spectrochimica Acta Part B: Atomic Spectroscopy, vol. 123, Sep. 2016.

Joseph A. Cruz, et al., "Applications of Machine Learning in Cancer Prediction and Prognosis", Cancer Informatics 2006: 2 59-78.

Yuri Markushin, et al., "Tag-femtosecond laser-induced breakdown spectroscopy for the sensitive detection of cancer antigen 125 in blood plasma", Anal Bioanal Chem (2015) 407:1849-1855.

Jerome H. Friedman, "Greedy Function Approximation: A Gradient Boosting Machine" IMS 1999 Reitz Lecture, Feb. 27, 1999.

P. Sivakumar, et. al., "An experimental observation of the different behavior of ionic and neutral lines of iron as a function of number density in a binary carbon-iron mixture", Spectrochimica Acta Part B 82 (2013) 76-82.

* cited by examiner

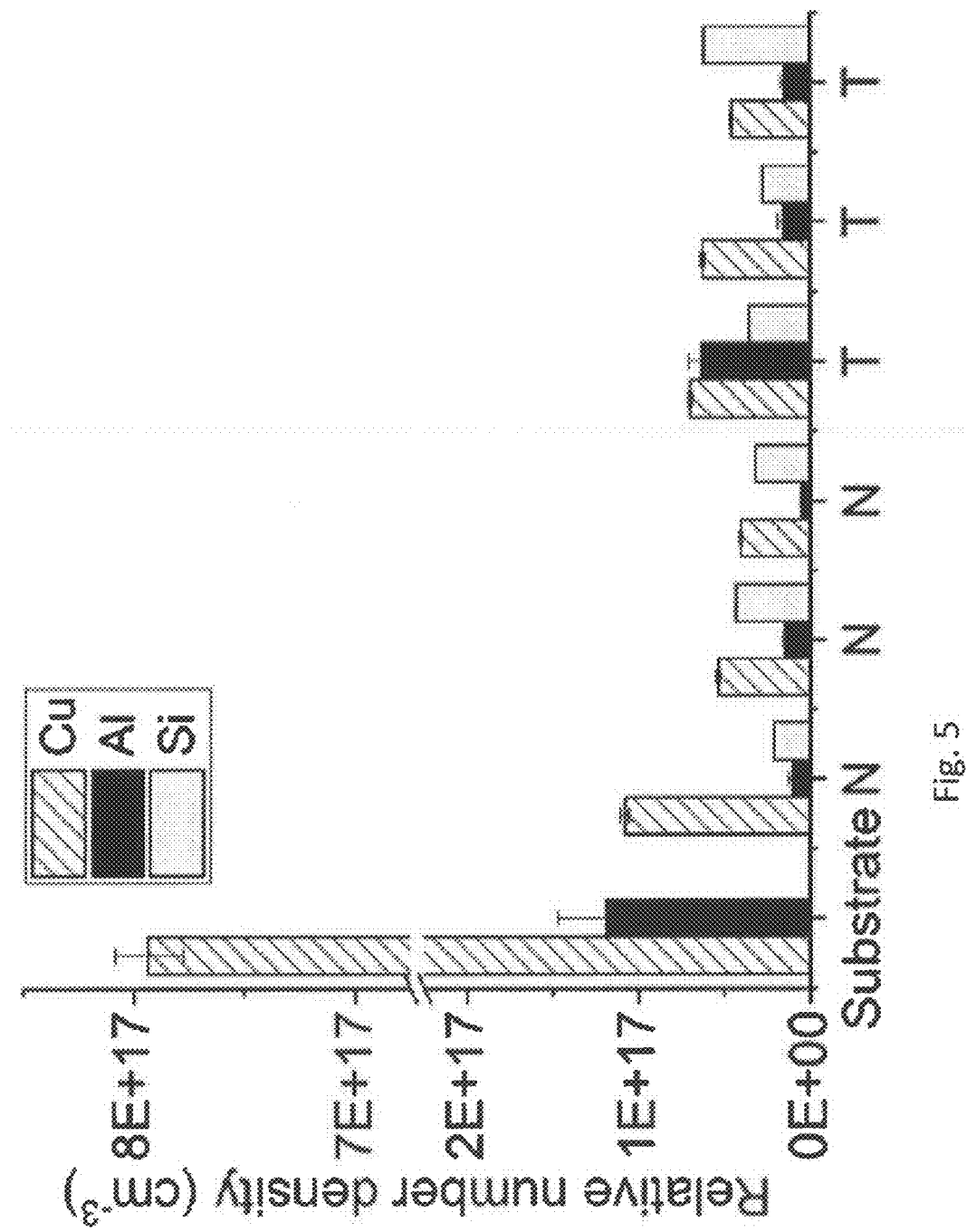

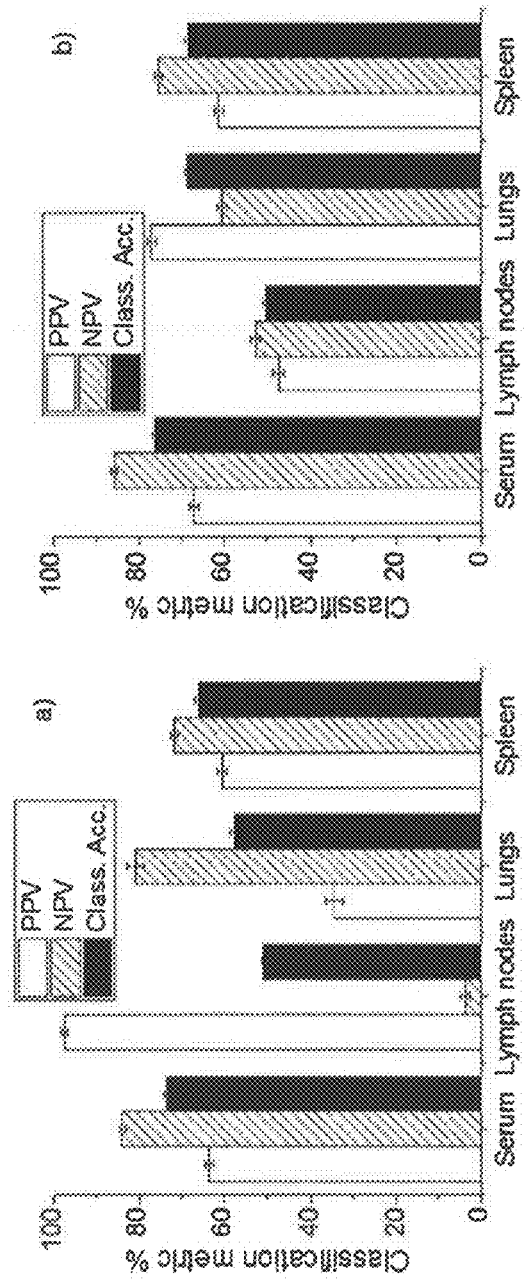
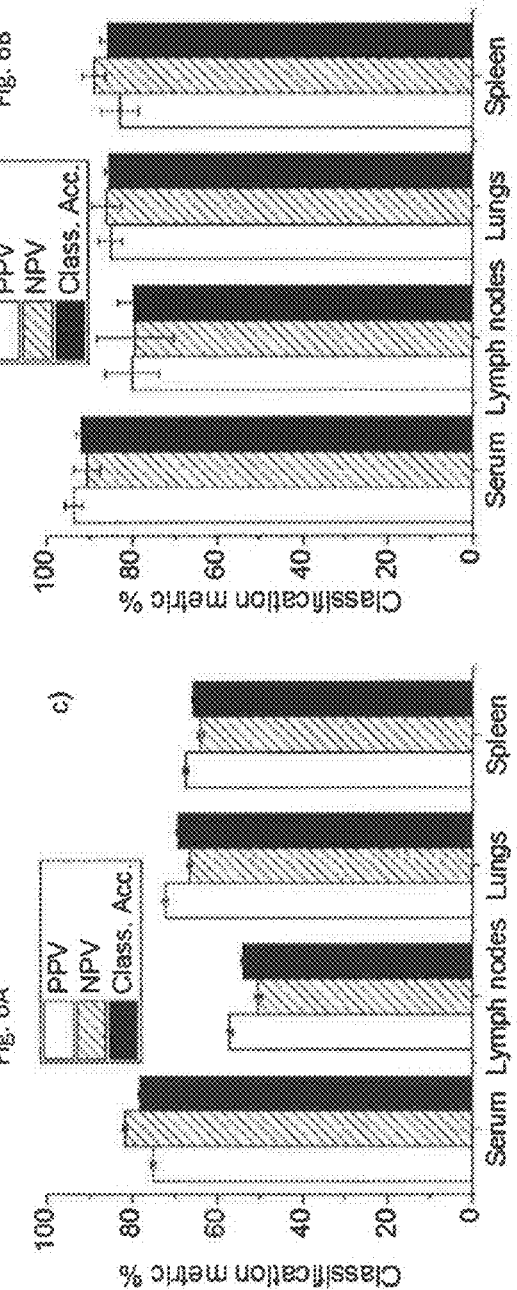
Fig. 6A
Fig. 6B
Fig. 6C
Fig. 6D

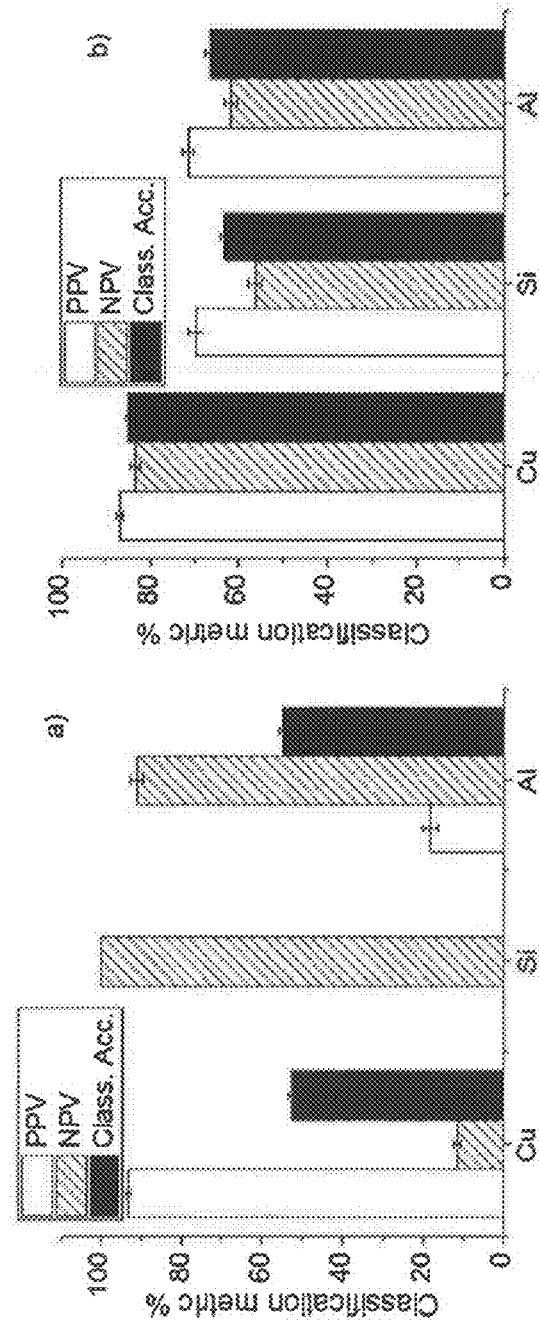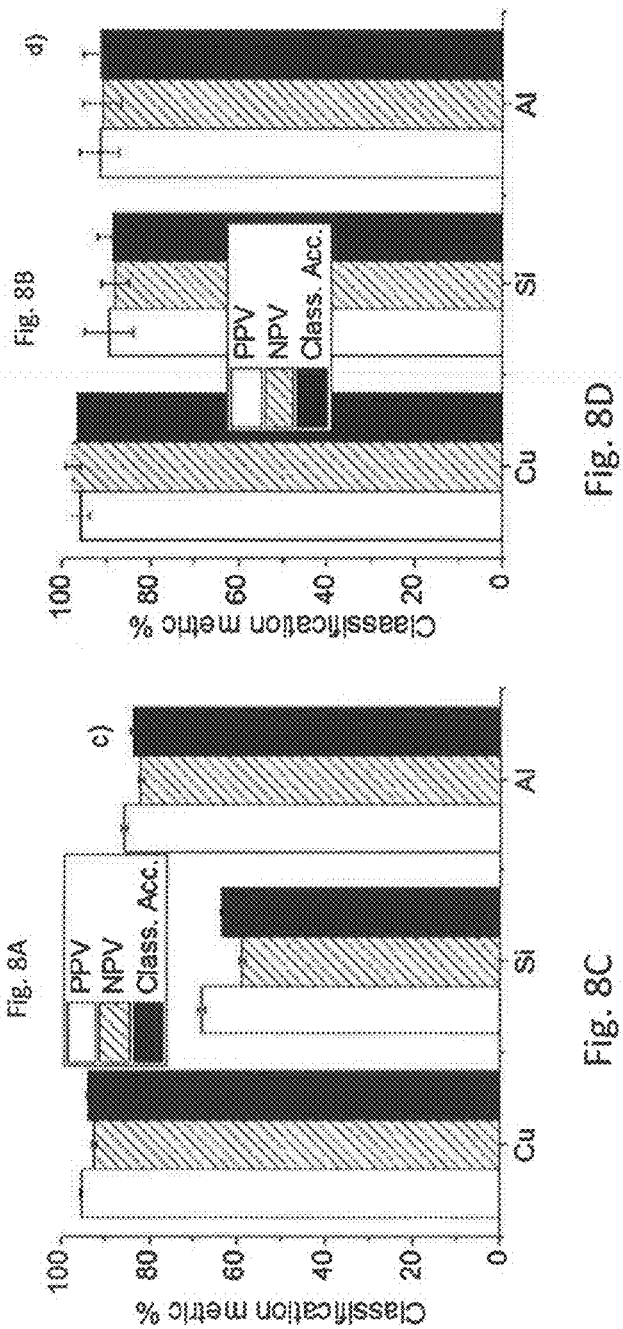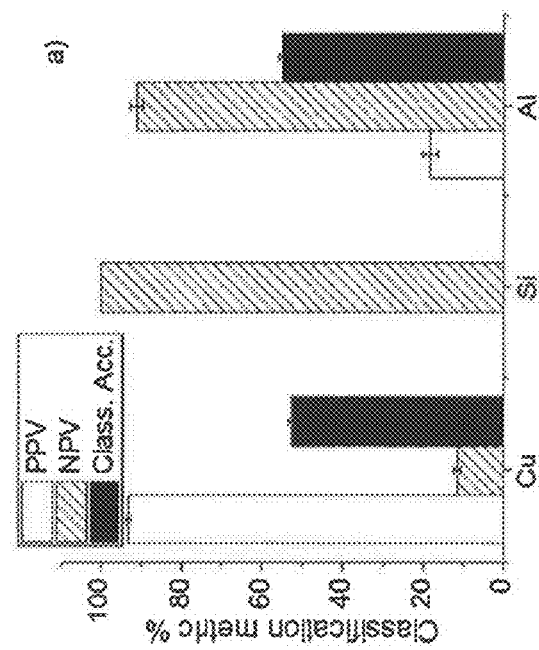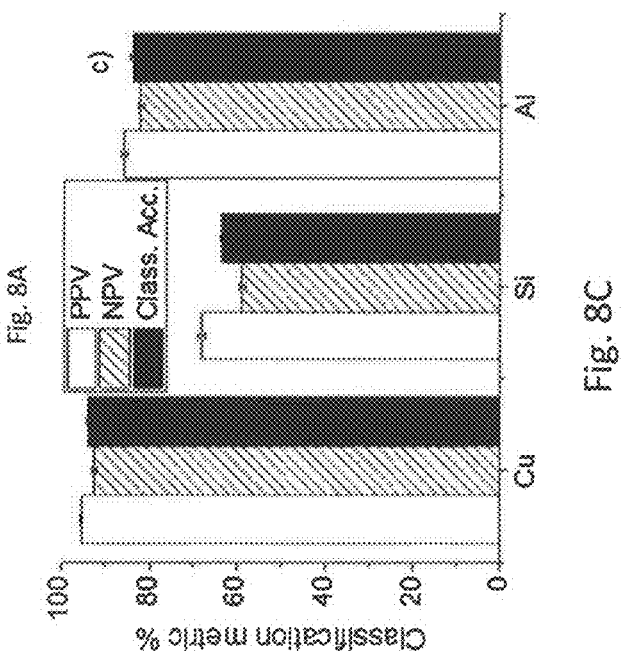

METHODS AND SYSTEMS FOR DIAGNOSING OR MONITORING PROGRESS OF A PATHOLOGY USING LASER INDUCED BREAKDOWN SPECTROSCOPY AND BIOLOGICAL FLUIDS

CROSS REFERENCE TO RELATED APPLICATIONS

This application claims priority to and benefit of U.S. Provisional Application No. 62/520,282, filed Jun. 15, 2017, entitled CANCER DIAGNOSIS USING LIBS AND MACHINE LEARNING TOOLS, which is incorporated by reference herein in its entirety for all purposes.

BACKGROUND

This invention relates generally to methods and systems for diagnosing or monitoring progress of a pathology and, more particularly, to methods and systems for diagnosing or monitoring progress of a pathology using laser induced breakdown spectroscopy (LIBS) and machine learning.

Outcomes are significantly improved if a pathology is detected early. Early detection can be related to noninvasive monitoring since patients are more likely to be monitored. A "liquid biopsy" provides a noninvasive path for determining an early diagnosis or monitoring progress for pathology.

One significant example is the early diagnosis or monitoring progress of cancer. Cancer indicates a class of diseases related to abnormal cell growth in one organ or tissue, with the potential to spread to other parts of the body. Many research and medical efforts are ongoing to efficiently diagnose and fight cancer, but the various forms of this disease are still one of the leading causes of death worldwide. Fighting cancer is very complex, in that it necessarily involves many different aspects, such as: investigating the causes of its onset; developing minimally invasive, targeted, and, in the future, personalized therapy approaches; promoting prevention practices; implementing screening tests for early diagnosis. The latter is a key task, as it is well-documented that detecting the onset of the disease during its early stage of development can significantly improve significantly the success of treatments and ultimately the survival rate and quality of life of patients. This issue is particularly critical for kinds of cancer that develop in the absence of specific symptoms and can go largely unnoticed until they metastasize, such as epithelial ovarian cancer (EOC), pancreatic cancer, and melanoma.

Developing large-scale screening tests is one of the most efficient strategies for early diagnosis of this kind of tumors. Ideally, such tests should be rapid and minimally invasive, user-friendly, accurate (low number of false positives and false negatives), and easy to integrate in point-of-care structures, so as to reach and monitor large numbers of people on a periodic basis. Laser-Induced Breakdown Spectroscopy (LIBS) is characterized by well-known practical advantages, which include limited sample preparation, fast multi-elemental response, compact instrumentation, possibility of in situ analyses, and versatility, all of which can contribute to making this technique a powerful tool in the fight against cancer Despite being essentially an atomic spectroscopy technique, and as such not an obvious choice for the diagnosis of diseases that proceed through an abnormal proliferation of cells, LIBS has proved useful to distinguish between biopsied cancerous tissues and adjacent healthy ones, thanks to differences in the content of trace elements. In particular, previous studies have almost consistently shown that cancerous lesions have a different alkaline and alkaline earth metals content than healthy tissues.

In N. Melikechi, Y. Markushin, D. C. Connolly, J. Lasue, E. Ewusi-Annan, S. Makrogiannis, Spectrochim. Acta B 123 (2016) 33, it was proposed for the first time to develop a LIBS-based "liquid biopsy" approach for the early detection of cancer, i.e. the analyzed samples were not tissues (either biopsied or harvested from laboratory animals), but sera. Femtosecond-LIBS spectra of mice sera taken from animals with EOC and healthy controls of three different age groups were acquired and deposited on a solid substrate. The LIBS spectra were then fed to two different classification algorithms that were shown to be useful for the discrimination of sera from mice with cancer and healthy ones with a maximum accuracy around 80%. Recently, Chen et al. have adopted essentially the same experimental and computational approach to the diagnosis of lymphoma and multiple myeloma in human serum, and have obtained classification accuracies close to 100% (X. Chen, X. Li, X. Yu, D. Chen, A. Liu, Spectrochim. Acta B 139 (2018) 63).

There is a need for systems and methods for diagnosing or monitoring progress of a pathology using laser induced breakdown spectroscopy (LIBS) and machine learning.

BRIEF SUMMARY

Systems and methods for diagnosing or monitoring progress of a pathology using laser induced breakdown spectroscopy (LIBS) and machine learning are disclosed herein below.

In one or more embodiments, the method of these teachings for diagnosing or monitoring progress of a pathology using laser induced breakdown spectroscopy (LIBS) and biological fluids includes depositing a sample of a predetermined biological fluid on a predetermined substrate, focusing light from a laser light source on the sample deposited on the predetermined substrate; energy and pulse length of the laser light source being configured to cause ablation of the sample and the predetermined substrate and forming of a plasma, collecting optical emission from the plasma, providing collected optical emission to a spectroscopic acquisition component; the spectroscopic acquisition component providing information on spectral data, providing the spectral data from the collected optical emission to a processing component; the processing component comprising one or more processors, and using a machine learning algorithm and the one or more processors to diagnose the pathology or monitor progress of the pathology, wherein the machine learning algorithm is trained on a training set comprising spectral data for LIBS collected optical emission from samples of the predetermined biological fluid on the predetermined substrate which have known pathology or known progress of the pathology, and wherein the predetermined substrate is configured to provide higher signal-to-noise ratio than other candidate substrates and to provide higher classification accuracy, obtained using the machine learning algorithm, of greater than a predetermined value.

In one instance, the predetermined biological fluid and pathology combination is one of the predetermined biological fluid being blood and the pathology being ovarian cancer, the predetermined biological fluid being blood serum and the pathology being melanoma, the predetermined biological fluid being cerebrospinal fluid and the pathology being Alzheimer's disease, the predetermined biological fluid being blood serum and the pathology being cardiovascular disease, the predetermined biological fluid being urine and the pathology being urinary tract cancer, or saliva and the pathology being lung and oral cancers.

In one or more embodiments, the system of these teachings includes a predetermined substrate; the predetermined substrate configured to have a sample of a predetermined biological fluid deposited on the predetermined substrate, a laser light source, a focusing optical subsystem configured to receive light from the laser light source and focus received light on the sample deposited on the predetermined substrate; energy and pulse length of the laser light source being configured to cause ablation and forming of a plasma in the sample and the predetermined substrate, a light collection optical subsystem configured to collect optical emission from the plasma, a spectroscopic acquisition component configured to receive collected optical emission from the light collection optical subsystem and to provide spectral data; the spectroscopic acquisition component comprising a spectrometer and a detector, a processing component configured to receive said spectral data from the spectroscopic acquisition component; the processing component comprising one or more processors, the one or more processors being configured to use a machine learning algorithm to diagnose the pathology or monitor progress of the pathology; wherein the machine learning algorithm is trained on a training set comprising spectral data for LIBS collected optical emission from samples of the predetermined biological fluid on the predetermined substrate which have known pathology or known progress of the pathology, wherein the predetermined substrate is configured to provide higher signal-to-noise ratio than other candidate substrates and to provide higher classification accuracy, obtained using the machine learning algorithm, of greater than predetermined value.

A number of other embodiments are also disclosed.

For a better understanding of the present teachings, together with other and further objects thereof, reference is made to the accompanying drawings and detailed description and its scope will be pointed out in the appended claims.

BRIEF DESCRIPTION OF THE DRAWINGS

FIG. 5 shows Relative number density of the matrix element; the transitions employed were: Cu I 330.80 nm, Al I 266.04 nm, Si 288.15 nm, and the spectroscopic parameters were obtained from the NIST database;

FIGS. 6A-6D show PPV, NPV and classification accuracy obtained with LDA a), FDA b), SVM c), and Gradient Boosting d) of the four biological fluids deposited on PVDF;

FIGS. 8A-8D show PPV, NPV and classification accuracy obtained with LDA a), FDA b), SVM c), and Gradient Boosting d) of serum deposited on Cu, Si, and Al;

DETAILED DESCRIPTION

Figure 1:
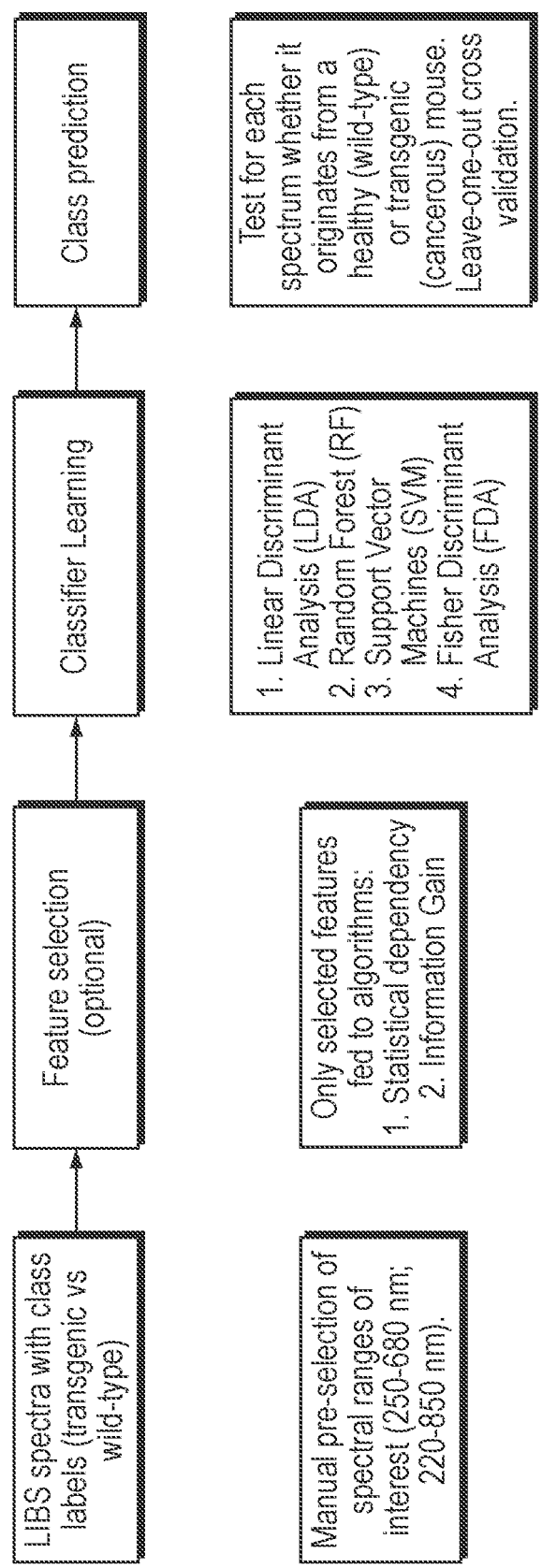
FIG. 1 is a flow diagram of one embodiment of the method of these teachings.

The following detailed description is not to be taken in a limiting sense, but is made merely for the purpose of illustrating the general principles of these teachings, since the scope of these teachings is best defined by the appended claims. Although the teachings have been described with respect to various embodiments, it should be realized these teachings are also capable of a wide variety of further and other embodiments within the spirit and scope of the appended claims.

As used herein, the singular forms "a," "an," and "the" include the plural reference unless the context clearly dictates otherwise.

"Light," as used herein, refers to electromagnetic radiation of wavelengths.

Systems and methods for diagnosing or monitoring progress of a pathology using laser induced breakdown spectroscopy (LIBS) and machine learning are presented herein below.

The "liquid biopsy" approach, demonstrated in N. Melikechi, Y. Markushin, D. C. Connolly, J. Lasue, E. Ewusi-Annan, S. Makrogiannis, *Age-specific discrimination of blood plasma samples of healthy and ovarian cancer prone mice using laser-induced breakdown spectroscopy*, Spectrochimica Acta Part B 123 (2016) 33-41 (hereinafter referred to as Melikechi) and in the exemplary embodiment shown here in below, for two different kinds of cancer (epithelial ovarian cancer and melanoma), is extended to the investigation of different pathologies, both for an early diagnosis and for monitoring the progress of the disease and of treatments, including surgery, all in a non- or minimally invasive fashion. Many pathologies can induce changes in the level of specific biomarkers in different parts of the human body, therefore different biological fluids can be harvested according to the kind of disease under investigation. The LIBS-based liquid biopsy coupled with machine learning, can thus be used to capture such changes in different fluids, both for diagnostic purposes and to support medical research on the addressed pathologies. Some examples include (although this is not an exhaustive list):

cerebrospinal fluid for the diagnosis of Alzheimer's disease;
blood for cardiovascular diseases;
urine for urinary tract cancers;
saliva for lung and oral cancers.

The first examples of this approach have demonstrated that the direct analysis of LIBS spectra may not be able to capture important differences between the diseased subjects and healthy controls. This is likely due to the nature of biomarkers, that are mostly organic molecules, and to the fact that, though small changes in the biomarker's concentration can be biologically meaningful, they are not necessarily able to induce important changes in the elemental composition of fluids, and therefore to be directly detected by an atomic spectroscopy technique such as LIBS. On the other hand, optimized supervised machine learning algorithms can enhance small spectroscopic differences and provide efficient discrimination.

The results presented in Melikechi and in the exemplary embodiment shown herein below indicate that the choice of an appropriate substrate for the deposition of biological fluids under examination is a crucial step for the success of the technique. An optimal laser-substrate coupling enables efficient breakdown of the deposited sample and of the underlying substrate, and is made possible by a combination of substrate properties and laser features. In the exemplary embodiment shown hereinbelow, the employed source was a 775-nm, 150-fs Ti:Sapphire laser, and the substrate that provided the highest signal-to-noise ratio and the best classification results was copper. Optimization of the laser-substrate coupling can involve testing further substrates, both pure materials and metal alloys, which will be selected based on four main physical properties: ionization energy; melting point; thermal conductivity; single-pulse ablation threshold. The metrics that will be employed to assess the coupling with the laser beam are: signal-to-noise ratio and classification performance of the machine learning methods coupled with the LIBS experiments.

Improvements in the laser-substrate coupling, and consequently in the classification performance, can also be made possible by exploiting changes in the physical and chemical properties of substrates, that can be induced and tailored through suitable surface modification. The latter can be either physical or chemical in nature (or both), and involve: deposition of organic or inorganic thin films; functionalization of the surface and/or the film; pre-irradiation with laser beams; texturing; any combination of the previous. Surface modifications can also be a key factor to optimize the fluid deposition procedure and ensure a homogeneous distribution within the treated area of the substrate prior to laser ablation. Homogeneity of the fluid distribution is expected to provide improvement of the signal stability and experiment reproducibility, which in turn can significantly contribute to better the overall performance of the technique and its acceptance in the medical community.

In one or more embodiments, the method of these teachings for diagnosing or monitoring progress of a pathology using laser induced breakdown spectroscopy (LIBS) and biological fluids includes depositing a sample of a predetermined biological fluid on a predetermined substrate, focusing light from a laser light source on the sample deposited on the predetermined substrate; energy and pulse length of the laser light source being configured to cause ablation of the sample and the predetermined substrate and forming of a plasma, collecting optical emission from the plasma, providing collected optical emission to a spectroscopic acquisition component; the spectroscopic acquisition component providing information on spectral data, providing the spectral data from the collected optical emission to a processing component; the processing component comprising one or more processors, and using a machine learning algorithm and the one or more processors to diagnose the pathology or monitor progress of the pathology, wherein the machine learning algorithm is trained on a training set comprising spectral data for LIBS collected optical emission from samples of the predetermined biological fluid on the predetermined substrate which have known pathology or known progress of the pathology, and wherein the predetermined substrate is configured to provide higher signal-to-noise ratio than other candidate substrates and to provide higher classification accuracy, obtained using the machine learning algorithm, of greater than a predetermined value.

In one instance, the predetermined biological fluid and pathology combination is one of the predetermined biological fluid being blood and the pathology being ovarian cancer, the predetermined biological fluid being blood serum and the pathology being melanoma, the predetermined biological fluid being cerebrospinal fluid and the pathology being Alzheimer's disease, the predetermined biological fluid being blood serum and the pathology being cardiovascular disease, the predetermined biological fluid being urine and the pathology being urinary tract cancer, or saliva and the pathology being lung and oral cancers.

In another instance, diagnosing the pathology or monitoring progress of the pathology includes: selecting features from the spectral data; and obtaining a diagnosis or monitoring progress of the pathology using the selected features.

A flowchart diagram of an embodiment of the method of these teachings is shown in FIG. 1. As shown there in, the feature selection occurs before the machine learning is applied to the obtained LIBS spectra. The samples analyzed include samples from normal subjects and samples from subjects with melanoma. A number of machine learning algorithms were tested. A list is given in FIG. 1 and also in the exemplary embodiment. It should be noted that these lists are not exhaustive, any available machine learning algorithm can be tested in order to arrive at the machine learning algorithm that provides the best results.

In one embodiment, the predetermined substrate is a surface modified substrate.

In the exemplary embodiment, the predetermined biological fluid is blood serum; and wherein the pathology is melanoma. In the exemplary embodiment, the machine learning algorithm was obtained using gradient boost methods. In the exemplary embodiment, the predetermined substrate is copper.

In one instance, the predetermined substrate is selected to provide higher classification accuracy, obtained using the machine learning algorithm, of greater than a predetermined value, where the predetermined value is greater than that of the other substrate candidates and greater than 70%.

In one embodiment, the machine learning algorithm was trained on a training set in which the diagnosis of the pathology was known.

Figure 3:
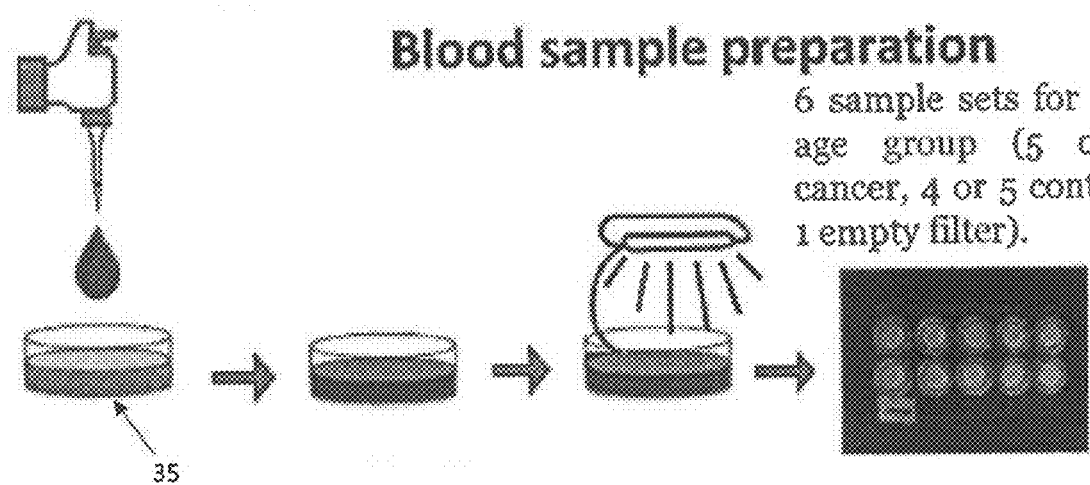
FIG. 3 is a graphical flow diagram representation of an embodiment of the sample preparation method of these teachings.

In one instance, a deposited sample is exposed to a predetermined lamp and dried for a predetermined time after depositing the sample of the predetermined biological fluid on the predetermined substrate. FIG. 3 is a graphical flow diagram representation of an embodiment of the sample preparation method. In the embodiment shown therein, one droplet of sample of about 5 μl volume is deposited on a substrate 35, the substrates with sample deposited are dried, and a number of substrates with the dried blood samples (from diseased and healthy mice) are placed on a plastic holder for LIBS analysis. In one instance, the substrates with sample deposited are dried using a 40-Watts Tungsten lamp (UL certified portable lamp, model 1400, DA) for 5 min.

In one or more embodiments, the system of these teachings includes a predetermined substrate; the predetermined substrate configured to have a sample of a predetermined biological fluid deposited on the predetermined substrate, a laser light source, a focusing optical subsystem configured to receive light from the laser light source and focus received light on the sample deposited on the predetermined substrate; energy and pulse length of the laser light source being configured to cause ablation of the sample and the predetermined substrate and formation of a plasma, a light collection optical subsystem configured to collect optical emission from the plasma, a spectroscopic acquisition component configured to receive collected optical emission from the light collection optical subsystem and to provide spectral data; the spectroscopic acquisition component comprising a spectrometer and a detector, a processing component configured to receive said spectral data from the spectroscopic acquisition component; the processing component comprising one or more processors, the one or more processors being configured to use a machine learning algorithm to diagnose the pathology or monitor progress of the pathology; wherein the machine learning algorithm is trained on a training set comprising spectral data for LIBS collected optical emission from samples of the predetermined biological fluid on the predetermined substrate which have known pathology or known progress of the pathology, wherein the predetermined substrate is configured to provide higher signal-to-noise ratio than other candidate substrates and to provide higher classification accuracy, obtained using the machine learning algorithm, of greater than a predetermined value.

Figure 2:
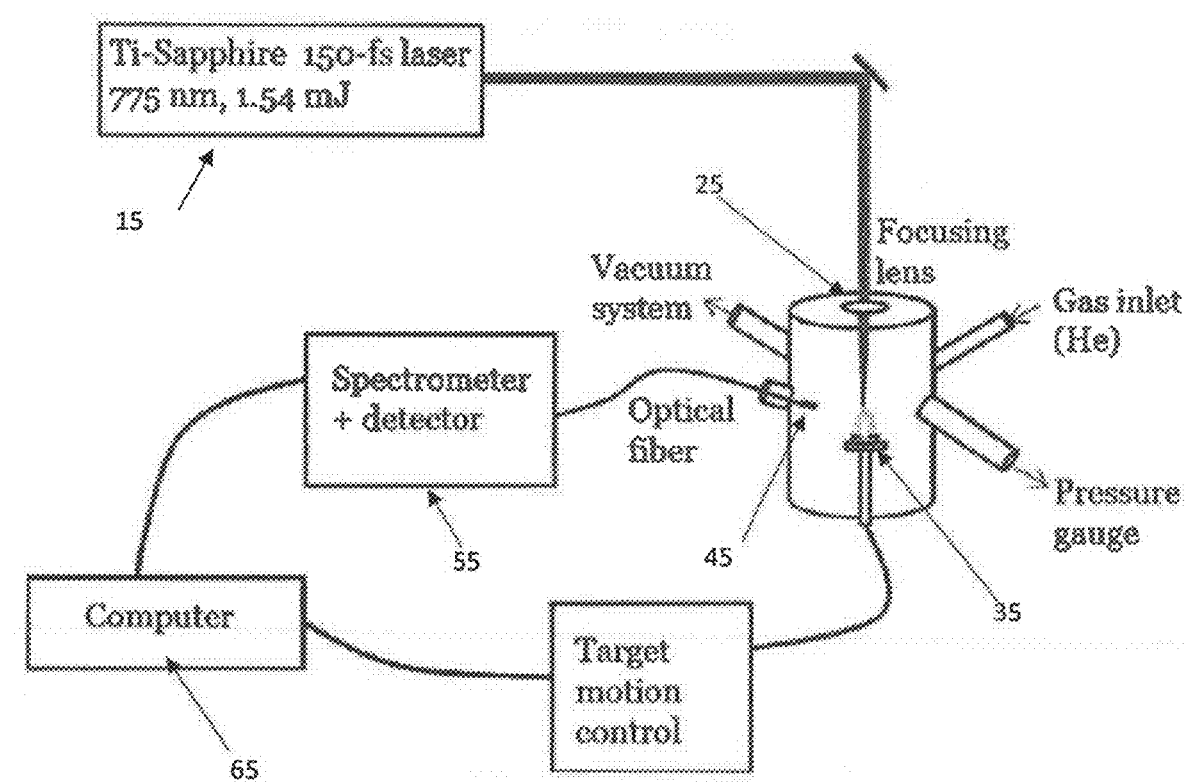
FIG. 2 is a graphical schematic representation of one embodiment of the system of these teachings.
Figure 10:
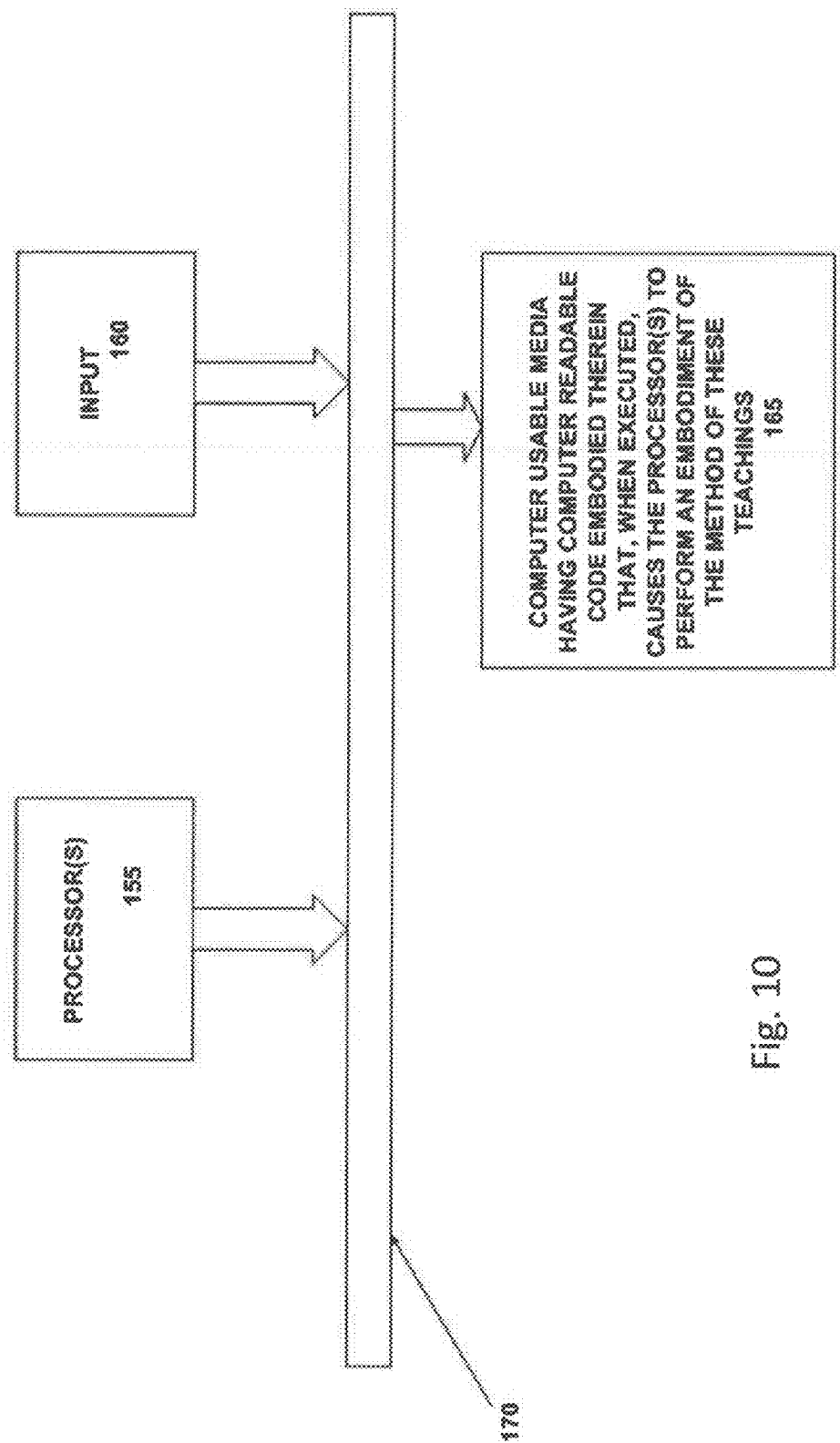
FIG. 10 shows an embodiment of a configuration of processors as used in these teachings.

FIG. 2 is a graphical schematic representation of one embodiment of the system of these teachings, Referring to FIG. 2, the embodiment shown therein, a laser 15 is focused on the sample surface 35 to generate a laser-induced micro plasma by using a focusing lens 25. Optical emission from the plasma is collected by a light collection component 45, such a fiber collimation lens, at 45° with respect to the laser beam and focused onto an optical fiber. The other end of the fiber was coupled into a spectroscopic acquisition component 55, having a spectrometer and a detector. A processing component (computer) 65 receives the spectral data from the spectroscopic acquisition component. One embodiment of the processing component 65 is shown in FIG. 10. (It should be noted that other embodiments using ASICs or FPGAs are also within the scope of these teachings.) Referring to FIG. 10, in the embodiment shown there in, one or more processors 155 are operatively connected by a 15 connection component 170 (such as a computer bus) to an input component 160 and to non-transitory computer usable media 165. The one or more processors 155 are configured to use a machine learning algorithm diagnose the pathology or monitor progress of the pathology; wherein the machine learning algorithm is trained on a training set comprising spectral data for LIBS collected optical emission from samples of the predetermined biological fluid on the predetermined substrate which have known pathology or known progress of the pathology by computer readable code embodied in the computer usable media 165.

It should be noted that training data sets and sample data that includes phenotypical data (including effects of environment and behavior) are within the scope of these teachings.

In one instance, the laser 15 is a Ti-Sapphire laser, a pulse length of emission from the laser is at most 500 femtoseconds, and the laser energy is between 1.6 mJ and 1.5mJ. (It should be noted that the scope of these teachings is not limited only to that pulse length and laser energy. By modifying the substrate or using different substrates, a range of pulse length even at the nanosecond level and a range of laser energies are within the scope of these teachings.) In the exemplary embodiment, a pulse length of 150 femtoseconds is used.

In order to further elucidate these teachings, an exemplary embodiment is presented herein below. It should be noted that these teachings are not limited to only that exemplary embodiment.

Exemplary Embodiment

In the exemplary embodiment, the plasma was produced by focusing a 150-fs Ti-Sapphire laser (Clark-MXR, Model 2210, wavelength=775 nm) on the samples, through a fused silica biconvex lens (focal length=50 mm, focused spot size=100 µm). The samples were mounted on a motorized and computer-controlled x-y translation stage (scanning speed=0.35 mm/s), to ensure that each laser shot would ablate a fresh surface. Measurements were performed in an experimental chamber filled with slight over-pressured He (762 Torr), in order to reduce the spectral interference from air elements and obtain a more persistent and bright plasma. The optical emission from the plasma was collected by a fiber collimation lens 45° with respect to the laser beam and focused onto a 50 µm core-diameter optical fiber, and coupled with the spectroscopic acquisition system. The latter comprised an Echelle spectrograph (Andor Technology, ME 5000) for wavelength dispersion and a thermoelectrically cooled iStar Intensified Charge Coupled Device (ICCD) camera for radiation detection (Andor Technology, DH734-18F O3). Spectra were acquired with 50 ns starting delay time after the laser pulse and 700 µs integration time.

Two different kinds of biological fluids were analyzed, obtained from mice with melanoma and healthy controls: blood serum and homogenates of three different tissues (lungs, spleen, lymph nodes), that were prepared following the protocols described later on.

In the first series of experiments, 5 µl drops of each of the biological fluids were deposited on PVDF membranes, and dried them for 10 min prior to the LIBS analysis, using a tungsten IR lamp. The laser energy used for this series of experiments was 1.44 mJ. In the second series of experiments, only one of the biological fluids (blood serum) was selected and studied the effect of different substrates on the LIBS spectra and classification accuracy. The sample preparation procedure was the same, and the three employed substrates were Cu, Al, and Si. Prior to depositing serum, the two metallic substrates were mechanically polished, and all three substrates were rinsed and sonicated in 2-propanol. The laser energy used for this series of experiments was 1.20 mJ. The laser energy was constantly monitored during the spectra acquisition, and spectra with intensity lower than a given threshold were automatically rejected, so as to improve the signal-to-noise ratio.

Sample Preparation

Mice

Mouse experiments were performed in accordance with institutional guidelines under a protocol approved by the Memorial Sloan Kettering Cancer Center (MSKCC) Institutional Animal Care and Use Committee. All mice were maintained in a pathogen-free facility according to the National Institutes of Health Animal Care guidelines. C57BL/6J mice (females, 6 to 10 weeks old) were purchased from The Jackson Laboratory.

Cell Line and Tumor Implantation

Mice were euthanized 2 weeks after tumor implantation, and four different tissues (lymph nodes; spleen; lungs; blood serum) were harvested from tumor-bearing or non-tumor-implanted mice. Blood serum was analyzed as such, while tissues were mechanically dissociated using a PowerGen 125 tissue homogenizer (Fisher Scientific) in a protein lysis buffer (LB), with the following composition: 0.01 M Tris-HCl, 0.15 M NaCl, 0.01 M MgCl2, 0.5% NP-40 in distilled water.

Results and Discussion

Previous LIBS studies for cancer diagnosis have almost consistently shown that cancerous tissues have a different elemental composition than healthy tissues, these differences being mostly due to the alkaline and alkaline earth metals content. Ca and Mg levels have usually been found to be higher in the cancer-affected areas, with at least four different kinds of tumor (colorectal cancer, breast cancer, canine hemangiosarcoma, and melanoma). An exception to this trend has been previously observed in M. Bonta, J. J. Gonzalez, C. D. Quarles Jr., R. E. Russo, B. Hegedus, A. Limbeck, J., Anal. At. Spectrom. 31 (2016) 252, where no Ca and Mg enrichment was found in Malignant Pleural Mesothelioma (MPM), but instead MPM tissues resulted to be enriched in P and O and depleted in Zn and Cu. Following these observations, it was desired to determine whether statistically meaningful differences would be detectable in the elemental composition of blood serum and tissue homogenates harvested from mice with melanoma and healthy controls.

In the exemplary embodiment, two approaches were used to evaluate LIBS-based liquid biopsy, i.e., to discriminate between samples harvested from healthy and diseased animals: the first was a classical LIBS approach, based on a direct comparison between emission intensity of spectra from diseased and healthy animals; the second was the use of supervised machine learning methods. In the following the results that were obtained with both approaches are described.

Direct Analysis of LIBS Spectra

Figure 1A:
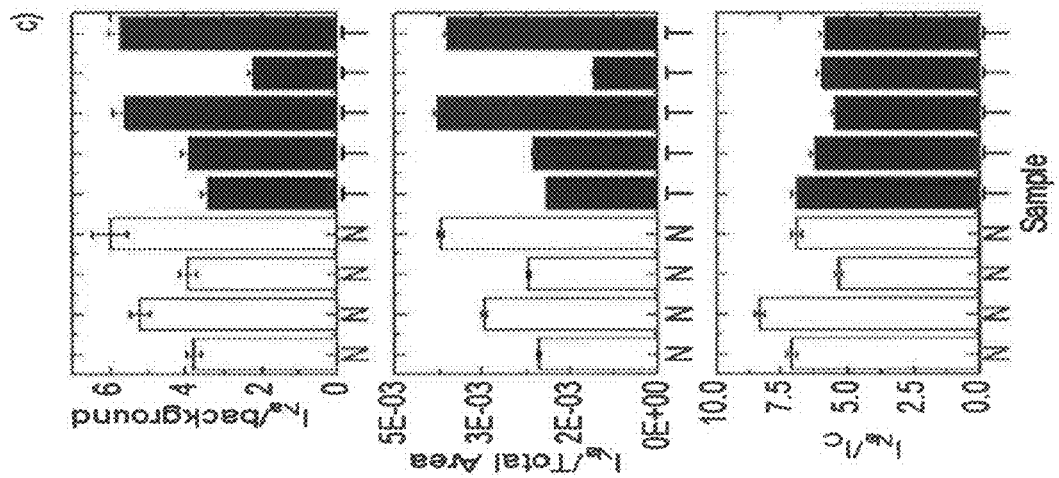
FIGS. 1A-1C show the comparison between three different normalization methods in an exemplary embodiment of the method of these teachings.
Figure 1B:
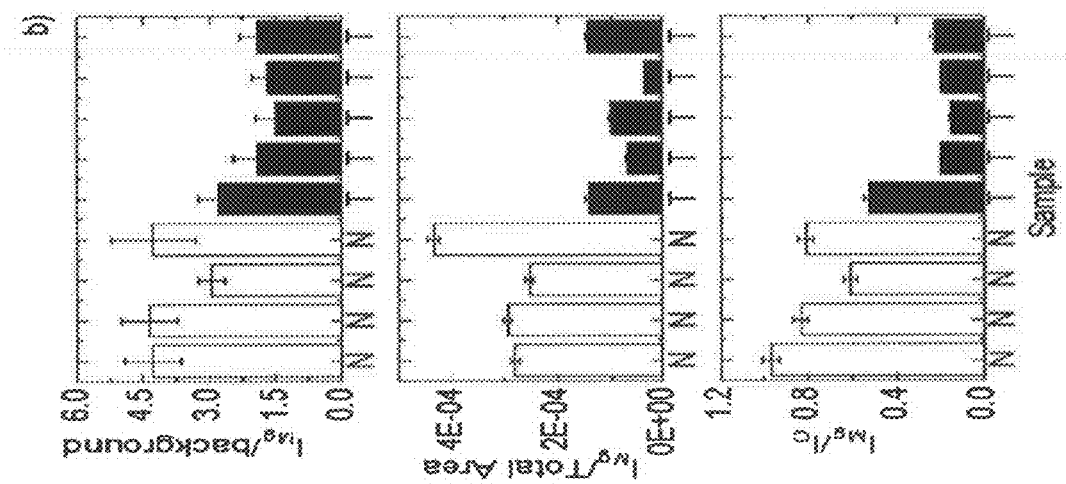
Figure 1C:
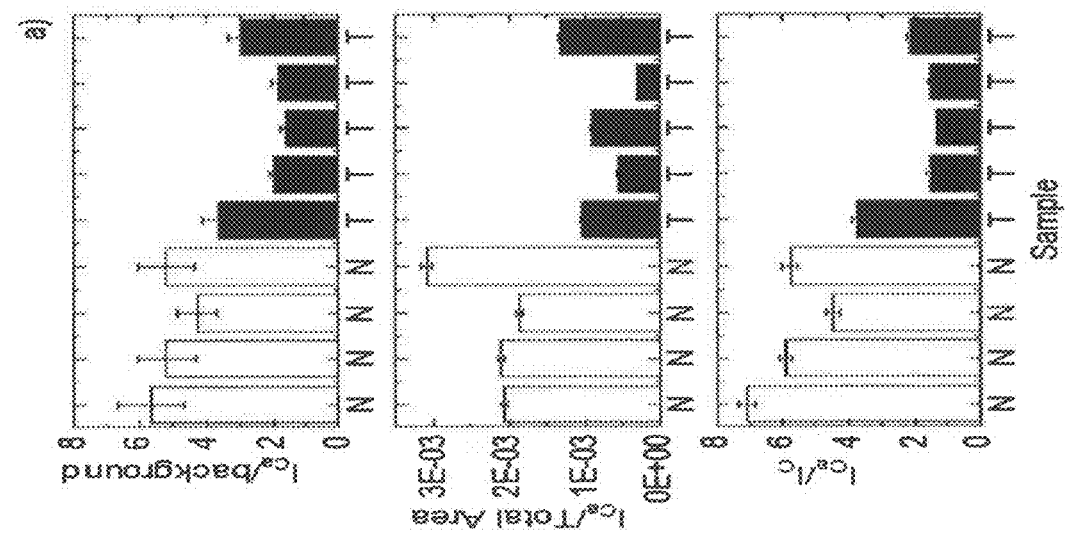

In a previous work focused on the LIBS analysis of melanoma tissues, it was shown that the content of Ca, Mg and Na was higher in melanoma tissues than in healthy skin. To test if biological fluids contain the same elemental signatures of the presence of the disease, the intensity of these analytes in the average spectra of each sample (blood serum and tissue homogenates) was measured. In the first series of data, serum and the three tissue homogenates were deposited on a polymeric substrate, PVDF.). Three intense resonance transitions (Na I 589.59 nm, Ca I 422.67 nm, Mg I 285.21 nm) were chosen and normalized them with three methods, i.e. dividing them by: 1) the background intensity in the spectral region adjacent to the peak; 2) the intensity of an element chosen as an internal standard (C, one of the main elements in biological samples); 3) the total integrated area of each average spectrum. All the figures refer to samples harvested from healthy mice with the letter N (for Normal), and to samples harvested from mice with melanoma with the letter T (for Tumor). FIG. 1A-1C report a comparison of the Ca I, Mg I and Na I intensity normalized with the three different methods in the spectra of serum. FIG. 1A-1C show that the three normalization methods lead to similar observations, i.e., that the intensity of Ca I and Mg I is slightly higher in some of the normal samples than in the tumor ones, while no trend is observable for Na I. The Ca and Mg trend is the opposite of that previously reported] for melanoma lesions and healthy skin, but in the present case the differences were not clear enough to be meaningful, or to enable a generalization leading to an unambiguous melanoma diagnosis. Discrepancies between the trace element content and accumulation in fluids (serum and homogenates of tissues not directly affected by the tumor) versus in biopsied cancer lesions may be expected. However, this specific aspect is beyond the scope of this work. In terms of normalization, as all three methods yield similar observations, in the following we report results obtained with only one of them: the result obtained by dividing by the total area of the spectra.

Figures 2A, 2B, 2C:
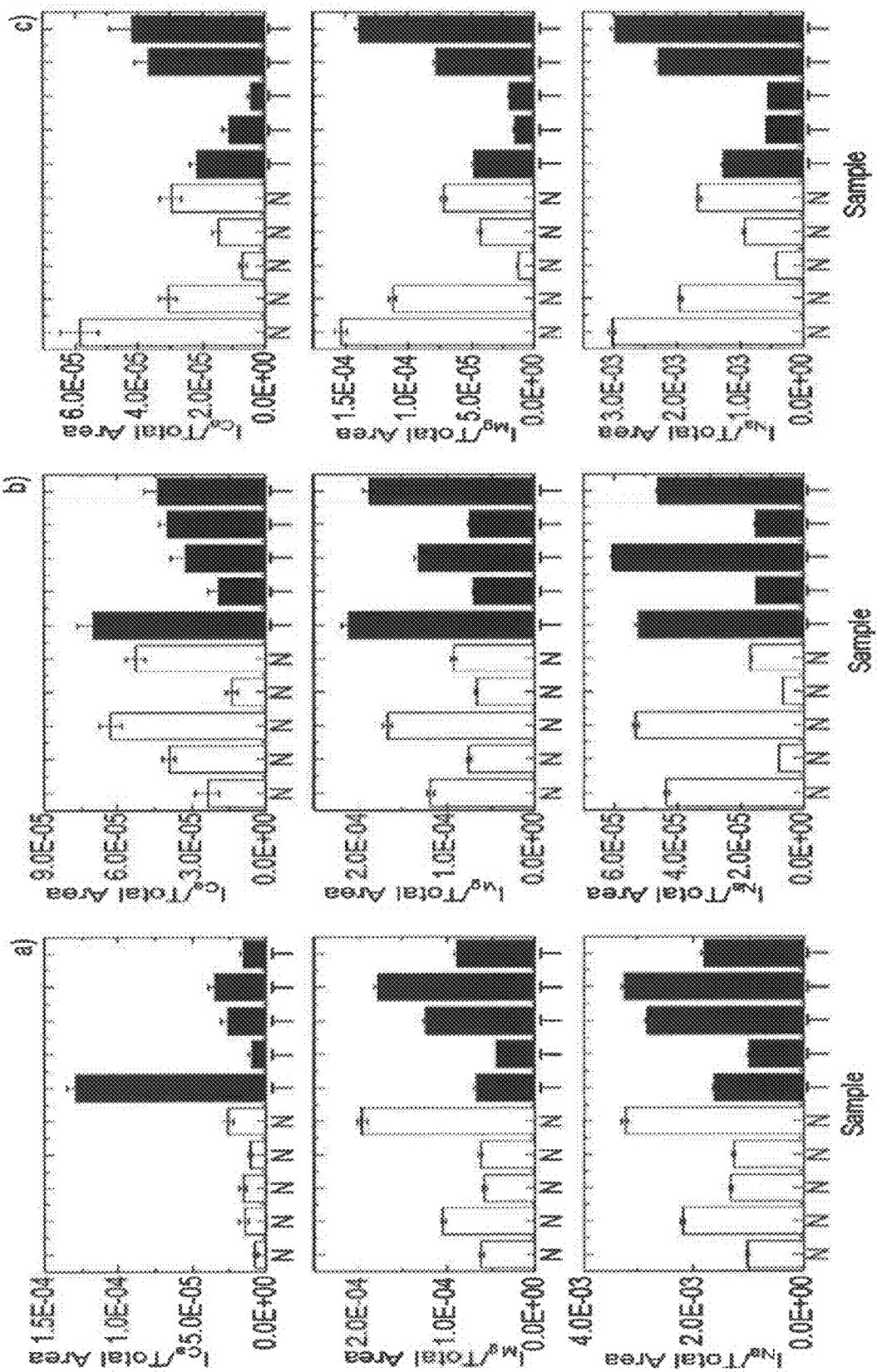
FIGS. 2A-2C show emission intensities of Ca I 422.67 nm, Mg I 285.27 nm, and Na I 589.59 nm normalized over the total integrated area of spectra of tissue homogenates deposited on PVDF for the exemplary embodiment, where (a) lungs, b) lymph nodes, c) spleen.
Figures 3A, 3B, 3C:
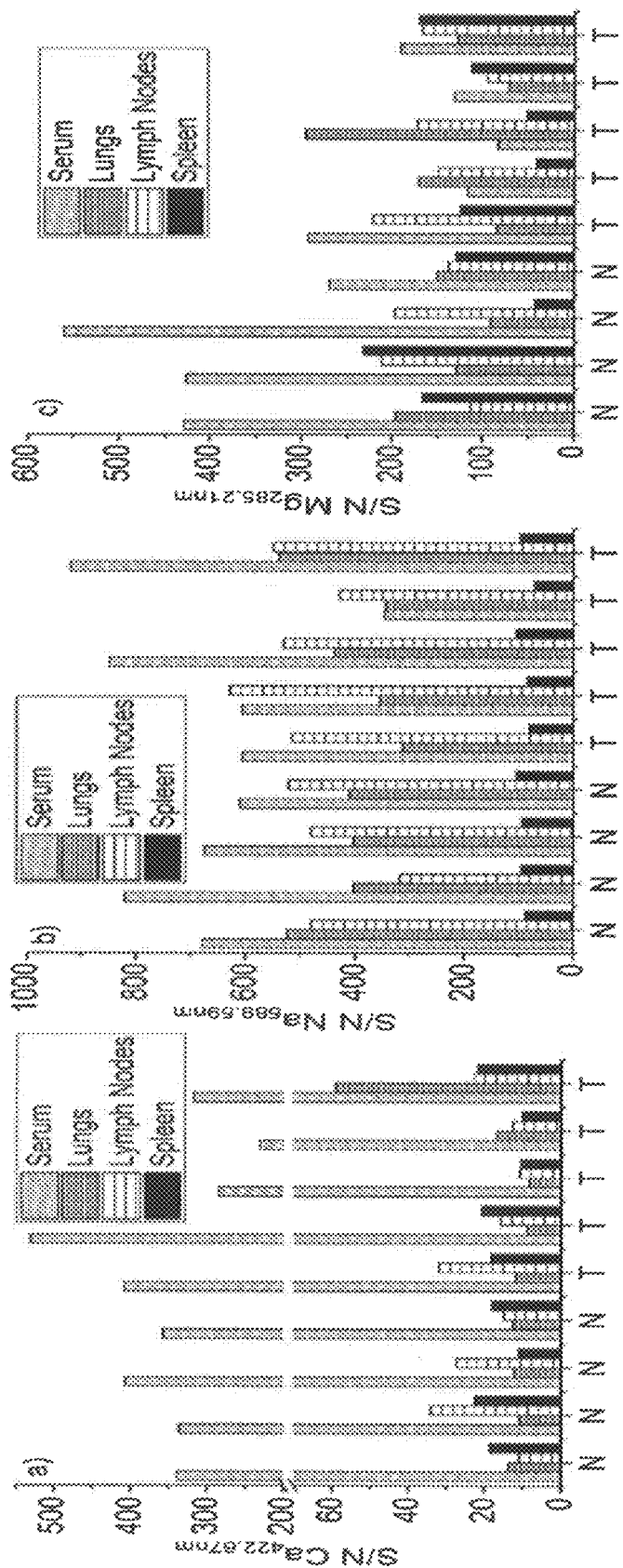
FIGS. 3A-3C show signal-to-noise (S/N) ratio of Ca I 422.67 nm a), Na I 589.59 nm b) and Mg I 285.21 nm c) in spectra of serum and homogenates of lungs, lymph nodes and spleen, deposited on PVDF; the letters N and T respectively indicate samples harvested from healthy mice and from mice with melanoma.

The results obtained for the tissue homogenates, shown in FIG. 2A-2C for the total area-normalized intensities, indicate that no statistically significant differences could be observed between healthy and tumor samples (analogous trends were found for C-normalized and background-normalized intensities, not reported here). Serum, on the other hand, enabled some discrimination between the two classes of samples. Moreover, as shown in FIG. 3A-3C, serum provided LIBS spectra with the highest signal-to-noise (S/N) ratio for most samples. This may be due to the fact that blood serum has a darker color than the other fluids, and is therefore more absorptive. This implies that its interaction with the laser radiation yields a more efficient breakdown and brighter plasma. Another possible reason could be that serum is richer in alkaline and alkaline earth metals (and Ca in particular) than other fluids. Since serum yielded the most intense spectra, we selected this fluid for investigation of the effect of substrates on the signal-to-noise ratio in LIBS spectra, and, consequently, the ability to discriminate between healthy and diseased animals. It is desired to establish whether changes in the solid substrate/laser beam coupling could further improve the signal to noise ratio. A new series of experiments were conducted using three different substrates i.e. Cu, Al, and Si, all having ionization energy lower than C, H and F, the components of PVDF. Using substrates with lower ionization energy, and thus lower ablation threshold, can allow operation in milder ablation conditions and can yield high-intensity spectra even when working with lower laser energy.

Figure 4:
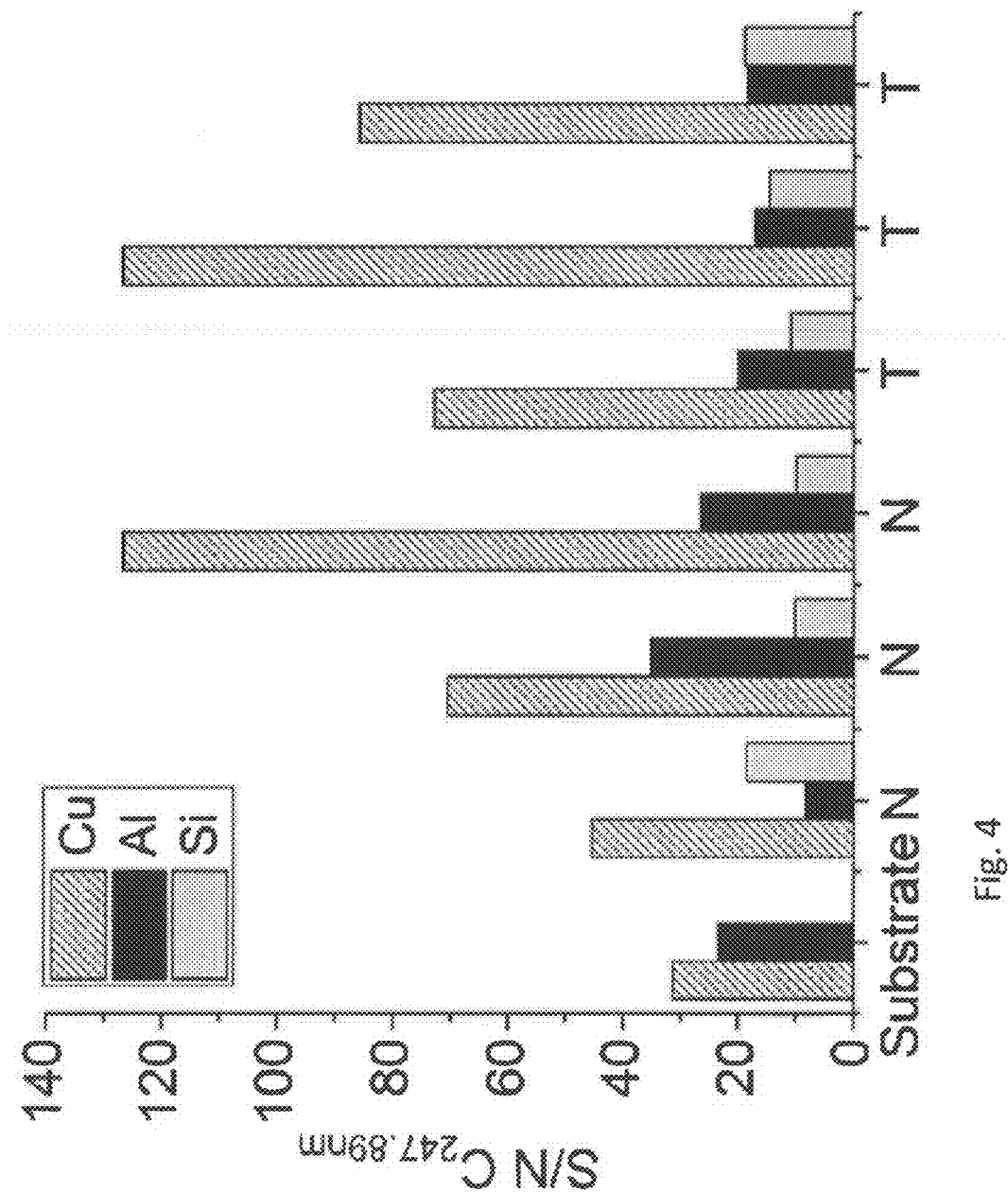
FIG. 4 shows Signal-to-noise (S/N) ratio of C I 247.86 nm in spectra of serum deposited on Cu, Si, and Al; the letters N and T respectively indicate samples harvested from healthy mice and from mice with melanoma.

To compare the three substrates, the S/N ratio of one C transition (247.86 nm) in the average spectra obtained for the three substrates was estimated, and reported it in FIG. 4. This shows that the target that provides the highest S/N ratio is Cu. This may appear contrary to the single-shot ablation thresholds reported in Table 1 (obtained in similar conditions to those used for this work), therefore a qualitative interpretation is provided to rationalize this apparent contradiction. Ultra-short laser ablation is often described as a non-thermal phenomenon, as opposed to the mostly thermal nanosecond-laser ablation. However, ultrashort ablation is characterized by two ablation regimes. The first occurs at low fluences, during which no evidence of thermal effects and melting is observed, the second at high fluences, during which a plasma forms, the ablation depth increases and thermal effects appear, even with single pulse ablation. In LIBS experiments, including the present one, the working ablation regime is the second, since an emitting plasma is formed. Table 1 shows that Al has lower ablation threshold, but also lower melting temperature and thermal conductivity than Cu and Si. This implies that, for this metal, thermal effects, such as the formation and accumulation of molten material in the laser-induced crater, and the consequent decrease of ablation efficiency, can play a significant role, even with ultrashort pulses. On the other hand, a comparison between Cu and Si shows that the formation of a Cu plasma can be facilitated by its lower ionization potential and higher thermal conductivity, which can reduce the impact of thermal effects despite a lower melting point. These observations can account for a higher ablation efficiency for Cu than for the other two substrates. The S/N ratio of species originating from solutions or fluids deposited on the target surface is related to the efficiency of laser/substrate coupling and to the amount of material ablated from the underlying substrate, which contributes to form and sustain the plasma. Therefore, this can account for the fact that the highest S/N ratio was observed with the target that can be ablated with the highest efficiency. Other effects such as those related to the surface conditions, in particular roughness, may affect the ablation efficiency by locally increasing the beam irradiance and reducing the sample reflectivity, as well as the distribution of the deposited fluids.

tions we used the Boltzmann distribution and the Saha equation, valid for plasmas in Local Thermodynamic Equilibrium (LTE), in order to determine, respectively, the relative number density of atoms and of ions of each species. The number densities are reported in FIG. 5. It shows that, with the sole exception of one sample, the number density of the matrix element is higher with the Cu substrate than with Al and Si, which is consistent with our interpretation of the S/N ratio trend.

TABLE 2 excitation temperature and electron density determined for the spectra of serum deposited on Cu, Al and Si substrates.

| | Cu series | | Al series | | Si series | |
|---|---|---|---|---|---|---|
| Sample | T (K) | $N_e \times 10^{17}$ (cm$^{-3}$) | T (K) | $N_e \times 10^{17}$ (cm$^{-3}$) | T (K) | $N_e \times 10^{17}$ (cm$^{-3}$) |
| Substrate | 7825 ± 487 | 3.9 ± 0.1 | 8143 ± 293 | 5.8 ± 0.1 | | |
| Normal | 7748 ± 617 | 4.2 ± 0.1 | 9005 ± 688 | 6.4 ± 0.1 | 6601 ± 125 | 4.7 ± 0.1 |
| Normal | 8335 ± 380 | 4.79 ± 0.09 | 7617 ± 542 | 5.8 ± 0.1 | 6696 ± 335 | 4.6 ± 0.1 |
| Normal | 7927 ± 565 | 4.8 ± 0.1 | 8079 ± 456 | 5.0 ± 0.1 | 6572 ± 358 | 5.1 ± 0.1 |
| Tumor | 8066 ± 577 | 5.14 ± 0.08 | 8298 ± 467 | 5.8 ± 0.1 | 6346 ± 297 | 5.3 ± 0.1 |
| Tumor | 8931 ± 374 | 4.85 ± 0.08 | 8377 ± 547 | 5.7 ± 0.1 | 6160 ± 61 | 4.7 ± 0.1 |
| Tumor | 8200 ± 513 | 5.54931 ± 0.08 | 8465 ± 440 | 5.7 ± 0.1 | 6425 ± 234 | 4.7 ± 0.2 |

TABLE 1 physical properties of Cu, Si and Al. In the ablation threshold column, the acronym SP indicates that the reported values refer to Single Pulse ablation.

| Element | Ionization energy (eV) | Melting point (K) | Thermal conductivity at 300 K (W/cm K) | Ablation threshold (J/cm$^2$) |
|---|---|---|---|---|
| Cu | 7.726 | 1358 | 4.01 | 0.86 250 fs, 800 nm, SP |
| Si | 8.152 | 1687 | 2.37 | 0.405 250 fs, 800 nm, SP |
| Al | 5.985 | 934 | 1.48 | 0.4 180 fs, 775 nm, SP |

The plasma parameters of the LIPs produced with the three substrates, were determined so to characterize the breakdown process in the three cases, as well as to investigate if the plasma parameters could provide additional insight to discriminate healthy and diseased subjects. Table 2 shows that no statistically significant differences could be observed between the plasma parameters of tumor and normal samples, and that the only actual differences could be ascribed to the different substrates. In particular, the plasma temperature obtained with the Si substrate is lower than those with the metal substrates, which can further account for the lower S/N observed for this target. Electron density, on the other hand, is highest for Al (the element with the lowest first ionization energy) than for the other substrates. In addition, we used the plasma parameters to calculate the relative number densities of the three matrix elements, so to qualitatively check our hypothesis of a higher ablation efficiency of the Cu substrate. For these additional calcula- Like in the series of experiments performed on PVDF, the normalized emission intensities of Ca, Na, Mg transitions did not provide un-ambiguous information that can be used to discriminate between healthy and diseased samples.

The Boltzmann distribution and Saha equation were used to determine the number densities of these analytes, in order to include in our count also the ionized fraction of each of the investigated species (all three of them being highly ionizable: EI Ca=6.11 eV; EI Mg=7.65 eV; EI Na=5.14 eV [22]). It is important to underline that the selected transitions are strong resonance ones, so they can be affected by self-absorption, even though the analytes are at trace levels. The relative number density results show that even with this correction, the differences between tumor and healthy samples do not appear meaningful. In particular, the Ca density results higher in tumor samples than in healthy ones, and though this observation is consistent with the literature about LIBS analysis of cancer tissues, and in particular of melanoma, we believe it is not necessarily meaningful, as it is not clearly detectable with the other substrates (in particular, as previously mentioned, an opposite trend was observed with the PVDF substrate). On the basis of this investigation, therefore, it can be concluded that, unlike what has been reported in the literature about the direct LIBS analysis of cancer tissues, it is not possible to reliably and unequivocally identify the presence of the disease in samples that are not cells or tissues affected by cancer.

Machine Learning Approach

The second part of exemplary embodiment establishes that machine learning tools applied to LIBS spectra can discriminate between healthy and diseased samples despite the fact that the direct analysis does not yield conclusive indications. Four algorithms were tested, with the intent to compare their performance and identify the most suitable for the present task: Linear Discriminant Analysis (LDA), Fisher Discriminant Analysis (FDA), Support Vector Machines (SVM) and Gradient Boosting.

Linear Discriminant Analysis (LDA) is a supervised learning approach that identifies the separating hyperplanes between different classes by assuming normal class-conditional distribution models (see, for example, Alaa Tharwat et al., Linear discriminant analysis: A detailed tutorial, AI Communications 00, IOS Press, 2017, which is incorporated by reference herein in its entirety and for all purposes). Features are projected to linear vector subspaces and then classified. The class of an unknown sample was determined by computing score values for the various classes using the score functions and data features, and the sample was assigned using maximum likelihood decision rules. Feature extraction was done using the statistical dependency (SD) between features and associated class labels with a quantized feature space (see, J. Pohjalainen, O. Rasanen, S. Kadioglu, Comput. Speech Lang. 29 (2013) 1, which is incorporated by reference herein in its entirety and for all purposes), in order to limit the contribution of non-discriminatory data points, reduce the dimensionality of the original dataset and avoid over fitting. FDA is a very similar learning approach to LDA, and is used for discrimination between two classes (see, for example, Max Welling, Fisher Linear Discriminant Analysis, which is incorporated by reference herein in its entirety and for all purposes). Support vector machines (SVM) is a discriminative classifier that distinguishes one class from another by finding an optimal hyperplane that maximizes the separation between the two classes (see, for example, Nikolay Stanevski, Dimiter Tsvetkov, Using Support Vector Machine as a Binary Classifier, International Conference on Computer Systems and Technologies—*CompSysTech*' 2005, which is incorporated by reference herein in its entirety and for all purposes). The members of both classes that are closest to the hyperplane serve as support vectors. The separating hyperplane is selected by optimizing the margin between the two classes. For data whose feature space is nonlinear, a kernel is used to transform the data into a linear space (T. Hastie, R. Tibshirani, J. Friedman, The Elements of Statistical Learning: Data Mining, Inference, and Prediction, Springer, New York, 2009, L. Liang, T. Zhang, K. Wang, H. Tang, X. Yang, X. Zhu, Y. Duan, H. Li, Appl. Opt. 53 (2014) 544, which are incorporated by reference herein in their entirety and for all purposes). In this work the support vector machine implementation within the Waikato Environment for Knowledge Analysis (WEKA) software with a second-degree polynomial kernel was used. A ten-fold cross validation was performed.

For LDA, FDA and SVM, the average spectrum of the clean PVDF substrate was subtracted from the spectra of the fluids deposited on the substrate itself. No substrate spectrum subtraction was done in the case of the Cu, Al, and Si substrates. In both cases, each spectrum with total integrated area that did not fall within one standard deviation about the average for the 100 shots were rejected, while the remaining were normalized by their total integrated area. All calculations were performed using MATLAB. The analysis was performed over the spectral range 250-680 nm to limit the computational cost while at the same time including the spectral region with the most meaningful spectral transitions.

Boosting is a machine learning meta-algorithm that combines a set of weak classifiers into a strong classifier. A weak classifier usually has a simple structure and performs only slightly better than random guessing. These weak classifiers are typically trained iteratively and ensembled in a special way (e.g., weighted according to their individual accuracy) to boost the overall performance of the classifier. We used the regression tree as the weak classifier in our experiments. The Gradient Boosting algorithm considers additive models of the following form:

$$F(x) = \sum_{m=1}^{M} \alpha_m h_m(x) \quad (1)$$

where $F(x)$ is the final model, $h_m(x)$ are the weak classifiers and $\alpha_m$ are the weights for each weak classifier determined by its performance. The additive model is built in a forward stage-wise fashion:

$$F_m(x) = F_{m-1} + \alpha_m h_m \quad (2)$$

At each stage, the model is trying to choose a model that satisfies the following equation:

$$y = F_i(x) + h_i \quad (3)$$

where y indicates the true classification of sample x, and $y - F_i(x)$ are called residuals. These are the parts that existing model is not able to calculate appropriately. In order to compensate for these residuals during each stage, the gradient boost model employs an iterative process for the construction of the additive model. At each iteration, the model attempts to choose a weak classifier that compensates the residuals of the existing model. Ultimately, this process minimizes the overall cost function.

In this work, feature selection and classification were performed with gradient boost models (see, for example, J. Friedman, Greedy Function Approximation: A Gradient Boosting Machine, Feb. 24, 1999 (modified Mar. 15, 2000, Apr. 19, 2001, which is incorporated by reference herein in its entirety and for all purposes). A simple model with 100 regression trees was used for feature selection. Each regression tree performs feature selection by choosing appropriate split points. Among all the regression trees, the more frequently a feature is used in the split points of a tree, the more important is the feature in the model. The importance of each feature (wavelength in the spectrum) in the data was obtained with this approach and we chose the features with higher importance in the classification. For classification, we implemented a more complicated gradient boost model with a larger number of regression trees. We changed the structure for each regression tree by increasing the minimum number of samples at leaf nodes to simplify each weak classifier, which can help reduce overfitting. We also use subsampling to enhance the performance of the model (J. Friedman, Comput. Stat. Data Anal. 38 (2002) 367, which is incorporated by reference herein in its entirety and for all purposes) as well, i.e. at each iteration, the base classifier is trained on a fraction of all training samples.

To rule out the possibility of mathematical artifacts and to optimize the algorithm itself in terms of its computational cost and accuracy, we performed some additional calculations with this method. Two series of calculations were run, the first using the spectra as such, the second removing the main spectral features of the matrix elements, so to evaluate and rule out the possibility of their having a role in the classification. The obtained results were practically identical, which indicates that the matrix features were not involved in the discrimination between cancerous and healthy samples, thus in the following we only report the one obtained without these features.

The results obtained with the four methods are expressed in terms of the following metrics: total classification accuracy, defined as the percentage of correctly classified samples from both classes (healthy/cancer); Positive Predictive Value (PPV), or sensitivity, defined as the percentage of samples correctly classified as cancerous; and Negative Predictive Value (NPV), or specificity, defined as the percentage of samples correctly classified as healthy. Our models were trained using all spectra acquired from all samples, and then tested with cross-validation sub-sets of different dimensions. This exemplary embodiment opted for cross-validation due to the limited number of available samples, though a better approach is an independent external validation, i.e. testing the models with data sets not included in the training set.

Classification Results

FIG. 6A-6D report the classification accuracy, NPV and PPV obtained with the first three series of data, i.e. with the four biological fluids deposited on PVDF, while the total classification accuracy values are reported in Table 2 for an immediate comparison.

Some considerations can be made based on the data of FIG. 6A-6D and Table 3. First, the classification accuracy varied substantially both with the analyzed fluid and with the algorithm selected. With the sole exception of the serum data, the accuracy of LDA, FDA and SVM was lower than 70% or, in some instances, even only slightly higher than 50% (a clear indication that in these cases the algorithms failed to provide any discrimination between the two classes.). On the other hand, Gradient Boosting had a much better performance, with accuracy of 80% or higher for all the samples. Interestingly, for all the algorithms the best classification accuracy was obtained with the serum sample, which is consistent with the results of the direct analysis of LIBS spectra and with the fact that the spectra obtained with this fluid provided spectra with higher S/N than the others (see FIG. 3A-3C)). The Gradient Boosting data reported in Table 3 and FIG. 6 were obtained using 100 spectral features and a 5-fold cross validation. The number of features was selected based on a preliminary optimization, which results we report in FIG. 7A). Here, classification accuracy obtained with the four fluids is plotted as a function of the number of features with 5-fold cross validation. Once the threshold of 100 features is exceeded, the increase in classification accuracy is moderate or absent, indicating that increasing further the number of features used for the calculation only increases its computational cost. Therefore, 100 features were selected as the best compromise between computational cost and classification accuracy.

TABLE 3 comparison of the classification accuracy obtained with four different algorithms and the spectra of the four biological fluids deposited on PVDF. (Gradient Boosting: 100 features).

| Sample | LDA | FDA | SVM | Gradient Boosting |
|---|---|---|---|---|
| Serum | 73.6 ± 0.6% | 76.3 ± 0.6% | 78.3 ± 0.2% | 92 ± 1% |
| Lymph node | 51.0 ± 0.2% | 50.0 ± 0.9% | 53.7 ± 0.5% | 80 ± 4% |
| Lungs | 57.6 ± 0.9% | 68.6 ± 0.6% | 69.4 ± 0.3% | 85.5 ± 0.8% |
| Spleen | 66.1 ± 0.7% | 68.3 ± 0.7% | 65.7 ± 0.3% | 86 ± 2% |

Figure 7B:
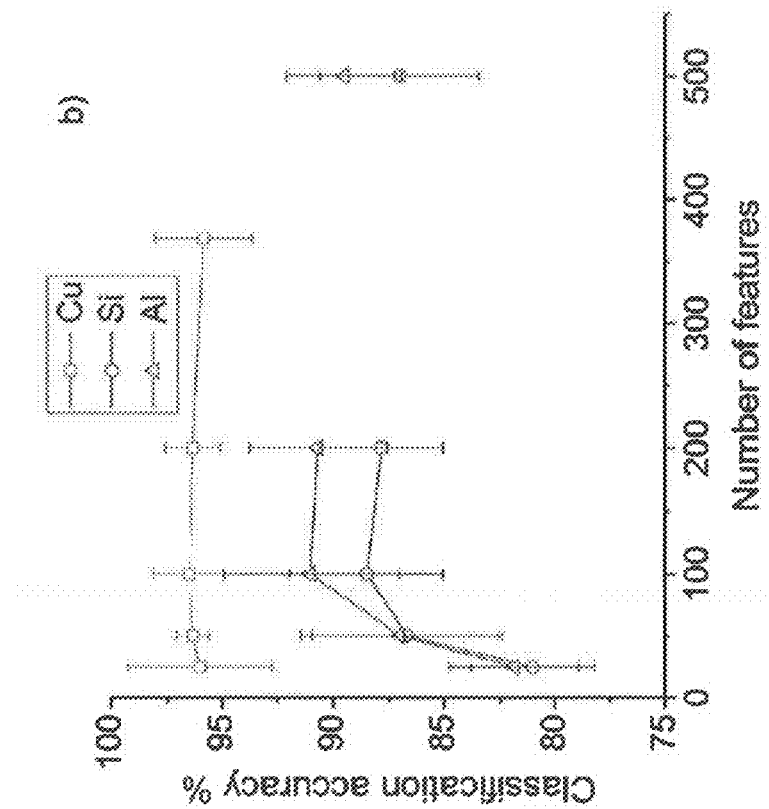
FIGS. 7A-7B show trend of classification accuracy obtained with gradient boost as a function of the number of features with 5-fold cross-validation for the two series of experiments: a) serum and tissue homogenates deposited on PVDF; b) serum deposited on Cu, Si, and Al.
Figure 7A:
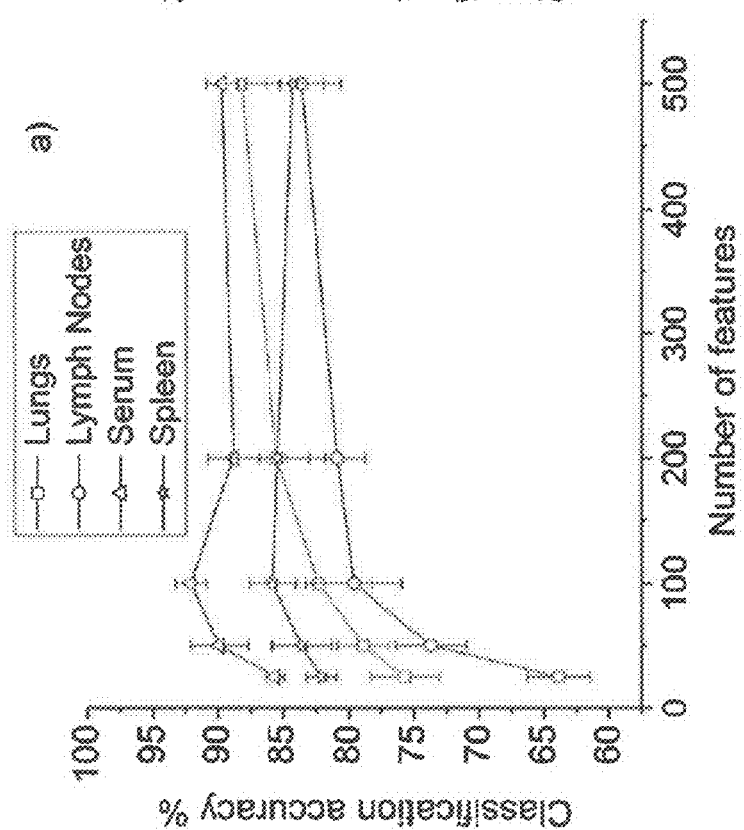

For the second series of data, i.e. spectra of serum deposited on Cu, Si and Al substrates, we performed an analogous preliminary optimization for gradient boost, and plotted the results in FIG. 7B). In this case, the plateau of classification accuracy was reached with 50 features, therefore in Table 4 and FIG. 8A-8D the results of LDA, FDA and SVM are compare with Gradient Boosting obtained with this optimal number of features (and 5-fold cross validation). For the Cu substrate, the maximum number of features extracted by the algorithm was 368, while for the other two substrates, up to 500 features could be extracted and used for the calculations.

TABLE 4 comparison of the classification accuracy obtained with serum deposited on the four different substrates. The following laser energy values were used: 1.2 mJ for Cu, Si, and Al; 1.44 mJ for PVDF (the PVDF data reported here for comparison were obtained with the same number of features as the ones calculated for the other substrates, i.e. 50, and a 5-fold cross-validation).

| Substrate | LDA | FDA | SVM | Gradient Boosting |
|---|---|---|---|---|
| Cu | 53.0 ± 0.5% | 85 ± 0.6% | 93.8 ± 0.3% | 96.3 ± 0.8% |
| Si | 50.4 ± 0.1% | 63.0 ± 1.1% | 63.3 ± 0.4% | 87 ± 4% |
| Al | 55.2 ± 0.7% | 66.4 ± 0.9% | 83.9 ± 0.5% | 87 ± 4% |
| PVDF | 73.6 ± 0.6% | 76.3 ± 0.6% | 78.2 ± 0.4% | 90 ± 2% |

Table 4 and FIG. 8 show that, while in the PVDF substrate series, LDA provides at least a modest classification accuracy with serum (and no classification with the other fluids), in the second series of experiments this algorithm is unable to classify with all three substrates, which makes it an unsuitable choice for the present task. The other algorithms, instead, show a net improvement in the classification accuracy, in particular with the Cu substrate, while Si provides the worst results, and Al and PVDF results are comparable. Analogously to what was previously observed (the four different fluids providing different S/N ratios), the fact that the Cu substrates provides the best classification accuracy can be reasonably related to its high S/N ratio, reported in FIG. 4. On the other hand, a direct comparison of the S/N ratio obtained with PVDF is not straightforward due to the different matrix and experimental conditions (C is a matrix element in PVDF, thus its normalized intensity may not be used to quantitatively compare the S/N ratio with the experiments on metals and Si). As already observed for the previous series, also for the series of serum deposited on Cu, Si and Al, the best classification accuracy is obtained with Gradient Boosting.

Figure 9:
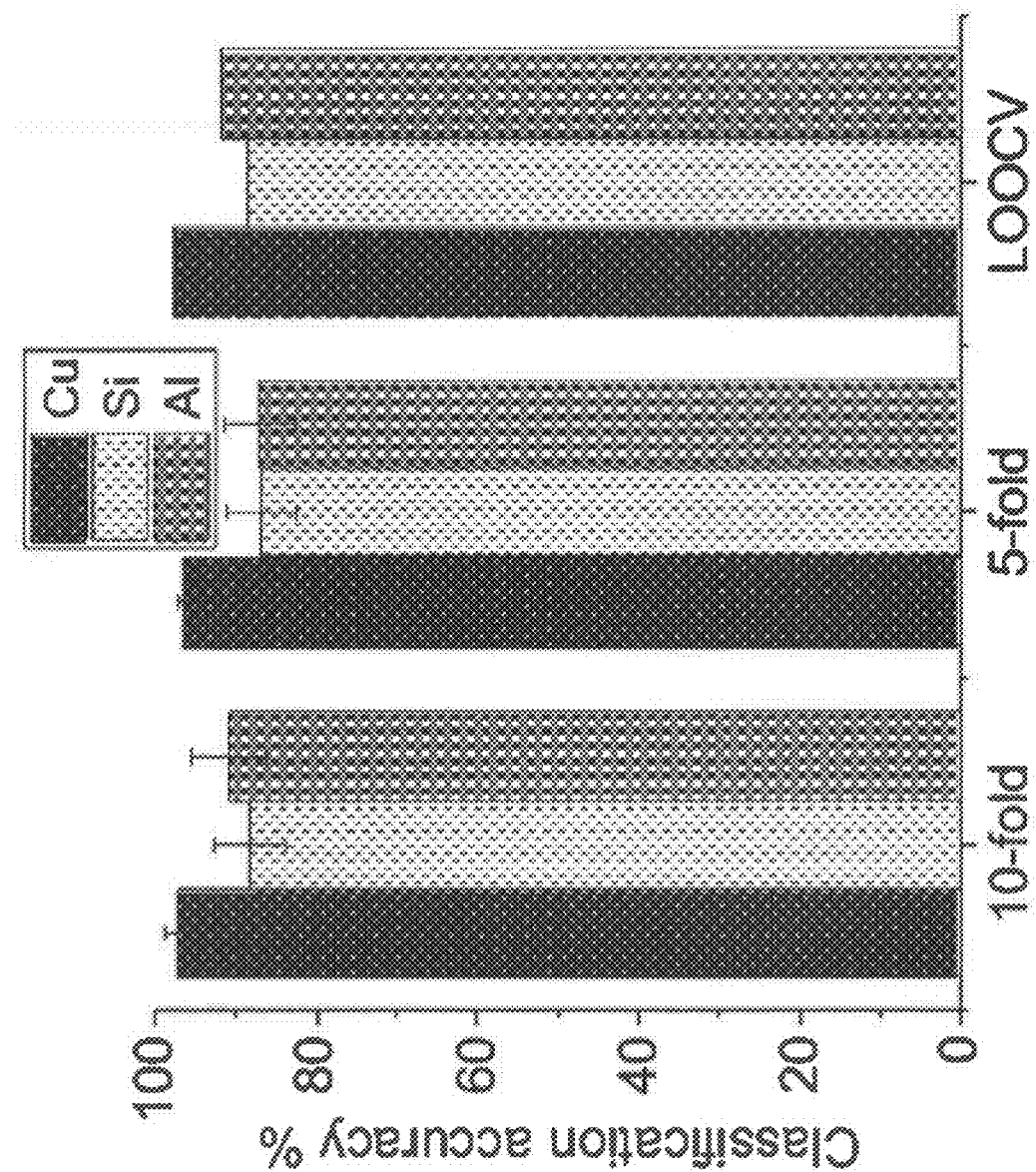
FIG. 9 shows Comparison between the classification accuracy obtained with Gradient Boosting and 10-fold, 5-fold, and LOO cross validation.

To optimize this algorithm in terms of finding the best compromise between computational cost (and thus speed), accuracy and precision, we made a final test, by changing the dimension of the subset for cross validation. FIG. 9 displays the classification accuracy obtained with the optimal number of features selected for the second series of experiments, 50, and three different cross validations, i.e. 10-fold, 5-fold and Leave-One-Out Cross Validation (LOOCV). FIG. 9 shows that the accuracy is virtually independent of the dimension of the subset used for cross validation, and therefore that using a 5-fold cross validation rather than a 10-fold may be a suitable choice to reduce the computational cost while still keeping high accuracy (but with a slight loss of precision). All the three cross validation methods lead to satisfactory results (>80%) with all three substrates, and Cu provides the best, with classification accuracy of 96%. These data prove that, even when the direct univariate LIBS analysis of biomedical samples with very similar spectral signatures did not provide conclusive results, statistical methods were able to identify and exploit the variability between the two classes, by efficiently processing large sets of data, and to successfully classify cancer and non-cancer samples. Moreover, these results demonstrate that the choice of the optimal substrate and algorithm can play a crucial role to obtain high classification accuracy.

The following are incorporated by reference herein in their entirety and for all purposes:

[1] B. W. Stewart, P. Kleihues (Eds.), World Cancer Report 2014, IARC Press, Lyon, 2003.

[2] R. L. Siegel, K. D. Miller, A. Jemal, C A Cancer J. Clin. 67 (2017) 7.
[3] A. El-Hussein, A. K. Kassem, H. Ismail, M. A. Harith, Talanta 82 (2010) 495.
[4] F. Ghasemi, P. Parvin, N. S. Hosseini Motlagh, A. Amjadi, S. Abachi, Appl. Opt. 55 (2016) 8227.
[5] A. Kumar, F. Yueh, J. P. Singh, S. Burgess, Appl. Opt. 43 (2004) 5399.
[6] J. H. Han, Y. Moon, J. J. Lee, S. Choi, Y. Kim, S. Jeong, Biomed. Opt. Express 7 (2015) 57.
[7] N. Melikechi, Y. Markushin, D. C. Connolly, J. Lasue, E. Ewusi-Annan, S. Makrogiannis, Spectrochim. Acta B 123 (2016) 33.
[8] X. Chen, X. Li, X. Yu, D. Chen, A. Liu, Spectrochim. Acta B 139 (2018) 63.
[9] H. Sadozai, T. Gruber, R. E. Hunger, M. Schenk, Front. Immunol. 8 (2017) 1617.
[10] T. H. Erlich, D. E. Fisher, G. Ital. Dermatol. Venereol. 1 (2018) 68.
[11] M. Bonta, J. J. Gonzalez, C. D. Quarles Jr., R. E. Russo, B. Hegedus, A. Limbeck, J. Anal. At. Spectrom. 31 (2016) 252.
[12] J. Cheng, C. Liu, S. Shang, D. Liu, W. Perrie, G. Dearden, K. Watkins, Opt. Laser Technol. 46 (2013) 88.
[13] N. N. Nedialkov, S. E. Imamova, P. A. Atanasov, J. Phys. D. Appl. Phys. 37 (2004) 638.
[14] A. Y. Vorobyev, V. M. Kuzmichev, N. G. Kokody, P. Kohns, J. Dai, C. Guo, Appl. Phys. A 82 (2006) 357.
[15] B. Le Drogoff, F. Vidal, Y. von Kaenel, M. Chaker, T. W. Johnston, S. Laville, J. Appl. Phys. 89 (2001) 8247.
[16] W. Perrie, M. Gill, G. Robinson, P. Fox, W. O'Neill, Appl. Surf. Sci. 230 (2004) 50.
[17] J. Krüger, P. Meja, M. Autric, W. Kautek, Appl. Surf. Sci. 186 (2002) 374.
[18] A. De Giacomo, C. Koral, G. Valenza, R. Gaudiuso, M. Dell'Aglio, Anal. Chem. 88 (2016) 5251.
[19] M. A. Aguirre, S. Legnaioli, F. Almodóvar, M. Hidalgo, V. Palleschi, A. Canals, Spectrochim. Acta B 88 (2013) 79-80.
[20] L. J. Radziemski, D. A. Cremers (Eds.), Laser-induced Plasmas and Applications, Marcel Dekker, New York, 1989.
[21] D. Bae, S.-H. Nam, S.-H. Han, J. Yoo, Y. Lee, Spectrochim. Acta B 113 (2015) 70.
[22] NIST database, https://www.nist.gov/pml/atomic-spectra-database, Accessed date: February 2018.
[23] D. R. Lide, Handbook of Chemistry and Physics, CRC Press, LLC, 2004.
[24] C. S. R. Nathala, A. Ajami, W. Husinsky, B. Farooq, S. I. Kudryashov, A. Daskalova, I. Bliznakova, A. Assion, Appl. Phys. A 122 (2016) 107.
[25] J. A. M. Van der Mullen, Phys. Rep. 191 (1990) 109.
[26] J. Pohjalainen, O. Rasanen, S. Kadioglu, Comput. Speech Lang. 29 (2013) 1.
[27] T. Hastie, R. Tibshirani, J. Friedman, The Elements of Statistical Learning: Data Mining, Inference, and Prediction, Springer, New York, 2009.
[28] L. Liang, T. Zhang, K. Wang, H. Tang, X. Yang, X. Zhu, Y. Duan, H. Li, Appl. Opt. 53 (2014) 544.
[29] E. Frank, M. A. Hall, I. H. Witten, The WEKA Workbench. Online Appendix for "Data Mining: Practical Machine Learning Tools and Techniques", fourth edition, Morgan Kaufmann, 2016, p. 2016.
[30] MATLAB Version 9.0.0, The MathWorks Inc., Natick, Mass., 2016.
[31] J. Friedman, Comput. Stat. Data Anal. 38 (2002) 367.
[32] S. Moncayo, S. Manzoor, F. Navarro-Villoslada, J. O. Caceres, Chemom. Intell. Lab. Syst. 146 (2015) 354.
[33] J. Gottfried, D. A. Cremers, L. Radziemski (Eds.), Handbook of Laser Induced Breakdown Spectroscopy, second edition, John Wiley & Sons, Ltd, 2013, pp. 223-241.
[34] R. Gaudiuso, E. Ewusi-Annan, N. Melikechi, X. Sun, B. Liu, L. F. Campesato, T. Merghoub, *Using LIBS to diagnose melanoma in biomedical fluids deposited on solid substrates: Limits of direct spectral analysis and capability of machine learning*, Spectrochimica Acta Part B 146 (2018) 106-114.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Although these teachings have been described with respect to various embodiments, it should be realized these teachings are also capable of a wide variety of further and other embodiments within the spirit and scope of the appended claims.

What is claimed is:

1. A method for diagnosing or monitoring progress of a pathology using laser induced breakdown spectroscopy (LIBS) and biological fluids, the method comprising:
depositing a sample of a predetermined biological fluid on a predetermined substrate;
focusing light from a laser source on the sample deposited on the predetermined substrate; energy and pulse length of the laser source being configured to cause ablation of the sample and the predetermined substrate and formation of a plasma;
collecting optical emission from the plasma using an optical detection system;
providing collected optical emission to a spectroscopic acquisition component; the spectroscopic acquisition component providing information on spectral data;
providing the spectral data from the collected optical emission to a processing component; the processing component comprising one or more processors;
using a machine learning algorithm and the one or more processors to diagnose the pathology or monitor progress of the pathology; wherein the machine learning algorithm is trained on a training set comprising spectral data for LIBS collected optical emission from samples of the predetermined biological fluid on the predetermined substrate which have known pathology or known progress of the pathology;
wherein the predetermined substrate has ionization energy lower than ionization energies of C or H and is also configured to provide higher signal-to-noise ratio than other candidate substrates with ionization energy lower than ionization energies of C or H and also configured to provide higher classification accuracy, obtained using the machine learning algorithm, of greater than a predetermined value.

2. The method of claim 1 wherein the predetermined biological fluid and pathology combination is one of the predetermined biological fluid being blood and the pathology being ovarian cancer, the predetermined biological fluid being blood serum and the pathology being melanoma, the predetermined biological fluid being cerebrospinal fluid and the pathology being Alzheimer's disease, the predetermined biological fluid being blood serum and the pathology being cardiovascular disease, the predetermined biological fluid being urine and the pathology being urinary tract cancer, or saliva and the pathology being lung and oral cancers.

3. The method of claim 1 wherein the predetermined substrate is a surface modified substrate.

4. The method of claim 1 wherein the predetermined biological fluid is blood serum; and wherein the pathology is melanoma.

5. The method of claim 4 wherein the machine learning algorithm was obtained using gradient boost methods.

6. The method of claim 5 wherein the machine learning algorithm was trained on a training set in which diagnosis of the pathology was known.

7. The method of claim 1 wherein the predetermined substrate is copper.

8. The method of claim 1 wherein the predetermined value is greater than 70%.

9. The method of claim 1 wherein a deposited sample is exposed to a predetermined lamp and dried for a predetermined time after depositing the sample of the predetermined biological fluid on the predetermined substrate.

10. The method of claim 1 wherein diagnosing the pathology or monitoring progress of the pathology comprises:
    selecting features from the spectral data; and
    obtaining a diagnosis or monitoring progress of the pathology using the features.

11. A system for diagnosing or monitoring progress of a pathology using laser induced breakdown spectroscopy (LIBS) and biomedical fluids, the system comprising:
    a predetermined substrate; the predetermined substrate configured to have a sample of a predetermined biological fluid deposited on the predetermined substrate;
    a laser source;
    a focusing optical subsystem configured to receive light from the laser source and focus received light on the sample deposited on the predetermined substrate; energy and pulse length of the laser source being configured to cause ablation of the sample and the predetermined substrate and formation of a plasma;
    a light collection optical subsystem configured to collect optical emission from the plasma;
    a spectroscopic acquisition component configured to receive collected optical emission from the light collection optical subsystem and to provide spectral data; the spectroscopic acquisition component comprising a spectrometer and a detector;
    a processing component configured to receive said spectral data from the spectroscopic acquisition component; the processing component comprising one or more processors;

the one or more processors being configured to use a machine learning algorithm to diagnose the pathology or monitor progress of the pathology; wherein the machine learning algorithm is trained on a training set comprising spectral data for LIBS collected optical emission from samples of the predetermined biological fluid on the predetermined substrate which have known pathology or known progress of the pathology;
    wherein the predetermined substrate has ionization energy lower than ionization energies of C or H and is configured to provide higher signal-to-noise ratio than other candidate substrates with ionization energy lower than ionization energies of C or H and also configured to provide higher classification accuracy, obtained using the machine learning algorithm, of greater than a predetermined value.

12. The system of claim 11 wherein the predetermined biological fluid and pathology combination is one of the predetermined biological fluid being blood and the pathology being ovarian cancer, the predetermined biological fluid being blood serum and the pathology being melanoma, the predetermined biological fluid being cerebrospinal fluid and the pathology being Alzheimer's disease, the predetermined biological fluid being blood serum and the pathology being cardiovascular disease, the predetermined biological fluid being urine and the pathology being urinary tract cancer, or saliva and the pathology being lung and oral cancers.

13. The system of claim 11 wherein the predetermined substrate is a surface modified substrate.

14. The system of claim 11 wherein the predetermined biological fluid is blood serum; and wherein the pathology is melanoma.

15. The system of claim 14 wherein the machine learning algorithm was obtained using gradient boost models.

16. The system of claim 15 where in the machine learning algorithm was trained on a training set in which the diagnosis of pathology was known.

17. The system of claim 16 wherein the predetermined substrate is copper.

18. The system of claim 11 wherein the predetermined value is greater than 70%.

19. The system of claim 14 wherein the laser light source is a Ti-Sapphire laser.

20. The system of claim 19 wherein a pulse length of emission from the laser is at most 500 femtoseconds.

21. The system of claim 20 wherein the energy of the laser light source is between 1.6 mJ and 1.2mJ.

22. The system of claim 11, wherein the predetermined substrate is selected based on physical properties comprising ionization energy; melting point; thermal conductivity; and single-pulse ablation threshold.

* * * * *